US005928902A

United States Patent [19]
De Wilde et al.

[11] Patent Number: 5,928,902
[45] Date of Patent: *Jul. 27, 1999

[54] HYBRID PROTEIN BETWEEN CS FROM PLASMODIUM AND HBSAG

[75] Inventors: Michel De Wilde, Glabais; Joseph Cohen, Brussels, both of Belgium

[73] Assignee: SmithKline Beecham Biologicals (s.a.), Rixensart, Belgium

[ * ] Notice: This patent issued on a continued prosecution application filed under 37 CFR 1.53(d), and is subject to the twenty year patent term provisions of 35 U.S.C. 154(a)(2).

[21] Appl. No.: 08/760,797

[22] Filed: Dec. 4, 1996

Related U.S. Application Data

[62] Continuation of application No. 08/442,612, May 17, 1995, abandoned, which is a continuation of application No. 08/244,085, filed as application No. PCT/EP92/02591, Nov. 11, 1992, abandoned, which is a continuation-in-part of application No. 07/842,694, Feb. 27, 1992, abandoned.

[51] Int. Cl.$^6$ .......................... C12P 21/06; A61K 39/00; A61K 39/29; C07K 14/00
[52] U.S. Cl. ................. 435/69.3; 424/184.1; 424/189.1; 424/192.1; 424/227.1; 424/272.1; 514/2; 530/350
[58] Field of Search ............................ 424/189.1, 184.1, 424/192.1, 227.1, 272.1; 514/2; 530/350; 435/69.3

[56] References Cited

U.S. PATENT DOCUMENTS

| | | |
|---|---|---|
| 4,722,840 | 2/1988 | Valenzuela et al. ................. 424/88 |
| 4,886,782 | 12/1989 | Good et al. ......................... 514/12 |
| 4,912,094 | 3/1990 | Myers et al. ........................ 514/54 |
| 5,112,749 | 5/1992 | Brey et al. ...................... 435/172.3 |
| 5,164,485 | 11/1992 | Yukio et al. . |
| 5,198,348 | 3/1993 | Bitter . |
| 5,395,614 | 3/1995 | Knapp et al. . |
| 5,436,139 | 7/1995 | Rutter et al. . |
| 5,614,194 | 3/1997 | Colman et al. . |

FOREIGN PATENT DOCUMENTS

| | | | |
|---|---|---|---|
| 596154 | 4/1990 | Australia .................. C07K 15/12 |
| 0 175 261 | 3/1986 | European Pat. Off. ........ C12P 21/02 |
| 0 278 940 | 8/1988 | European Pat. Off. ........ C12N 15/00 |
| 0 343 460 | 11/1989 | European Pat. Off. .......... C07K 7/08 |
| 0 357 208 | 3/1990 | European Pat. Off. ...... A61K 39/112 |
| WO 88/10300 | 12/1988 | WIPO .................. C12N 15/00 |
| WO 90/00402 | 1/1990 | WIPO .................. A61K 39/00 |

OTHER PUBLICATIONS

Neurath et al. 1984. Science 224:392–395.
Valenzuela et al. 1979. Nature. 280:815–819.
Herrington et al. 1987. Nature 328:257–259.
Rutgers et al. 1988 Bio/Technology 6:1065–70.
Veseden et al. 1991. Am J. Trop. Med. Hyg. 45(5):533–38.
Hoffman et al. 1987. Science. 237:639–642.
Cox. 1991. TIBTECH. 9:389–394.
Hoffman et al. 1993. In. Molecular Immunol. Considerations in Malarial Vaccine Dev. Ed. Good & Saul. pp. 149–167.
Charsenvit et al. 1991. Science. 251:668–671.
Butcher. 1989. Parasitology 98:315–327.
Smith et al. 1988. Technological Advances in Vaccine Development. pp. 651–659.
Lowell et al. 1988. Science. 240:800–802.
Romero, 1992. Current Opinion in Immunol, 4:432–441.
Schödel et al, 1996, J. Biotechnology, 44:91–96.
Schödel, et al, 1996, Adv. in Exptal. Med. & Biol. 397:15–21.
Bathurst. 1994, Am. J. Trop. Med & Hyg., 50(4) Suppl.:20–26.
Stoute et al, 1997, New Eng. J. Med. 336:86–91.
Caspers et al., "The Circumsporozoite Protein Gene From NF54, a *Plasmodium falciparum* Isolate Used in Malaria Vaccine Trials", *Molecular and Biochemical Parasitology*, vol. 35, pp. 185–190 (1989).
Cheng et al., "Expression of Malaria Circumsporozoite Protein and Hepatitis–B Virus Surface Antigen by Infectious Vaccinia Virus", *Vaccines 86 New Approaches to Immunization*, Eds. Fred Brown et al., pp. 165–168 (1986).
de Wilde et al., "Production of Viral Antigens in Yeast . . . Saccharomyces Cerevisiae", *8th Int. Biotechnol. Symp.*; (1988) Pt. 2, p. 695 (Conference Abstract).
Luciw et al., "Antigen Presentation by Way of Hepatitis B Virus Surface . . . Parasite Antigens", *Mod. Approaches Vaccine*, (1985) Meet., 60 (Conference Abstract).
Rutgers et al., "Hepatitis B Surface Antigen as Carrier Matrix for the Repetitive Epitope of the Circumsporozoite Protein of *Plasmodium falciparum*", *Bio/Technology*, vol. 6, pp. 1065–1070 (1988).
G. Smith and B. Moss, "Vaccinia Virus Recombinants as Live Vaccine Against Hepatitis B Virus and Malaria", *Vaccinia Virus Vector Vaccine Antigen*; (1985) pp. 129–136 (Conference Abstract).
von Brunn et al., "Epitopes of the Human Malaria Parasite *P. falciparum* Carried on the Surface of HbsAg Particles Elicit an Immune Response . . . the Parasite", *Vaccine*, vol. 9(7), pp. 477–484 (1991).
Young et al., "Expression of *Plasmodium falciparum* Circumsporozoite Proteins in *Escherichia coli* for Potential Use in a Human Malaria Vaccine", *Science*, vol. 228, pp. 958–962 (1985).
White, et al., "Induction of Cytolytic Cells by Recombinantly Co–Expressed Circumsporozoite Protein Fragment of *Plasmodium Falciparum* and Hepatitis B Particles", *American Journal of Tropical Medicine and Hygiene*, vol. 47, No. 4 SU, pp. 96–97 (1992) (Conference Abstract).
Mar. 6, 1991 Response to a communication from the European Patent Office Examining Division, pp. 1–6.

*Primary Examiner*—Nita Minnifield
*Attorney, Agent, or Firm*—Kirk Baumeister; Charles M. Kinzig

[57] ABSTRACT

A novel hybrid protein is provided which comprises a portion of the CS protein of *P. falciparum* and the surface antigen of Hepatitis B virus. The use of this protein for vaccination purposes is disclosed.

43 Claims, 21 Drawing Sheets

```
        10                    30                    50
         .                     .                     .
AAGCTTACCAGTTCTCACACGGAACACCACTAATGGACACAAATTCGAAATACTTTGACC
        70                    90                   110
         .                     .                     .
CTATTTTCGAGGACCTTGTCACCTTGAGCCCAAGAGAGCCAAGATTTAAATTTTCCTATG
       130                   150                   170
         .                     .                     .
ACTTGATGCAAATTCCCAAAGCTAATAACATGCAAGACACGTACGGTCAAGAAGACATAT
       190                   210                   230
         .                     .                     .
TTGACCTCTTAACTGGTTCAGACGCGACTGCCTCATCAGTAAGACCCGTTGAAAAGAACT
       250                   270                   290
         .                     .                     .
TACCTGAAAAAAACGAATATATACTAGCGTTGAATGTTAGCGTCAACAACAAGAAGTTTA
       310                   330                   350
         .                     .                     .
ATGACGCGGAGGCCAAGGCAAAAAGATTCCTTGATTACGTAAGGGAGTTAGAATCATTTT
       370                   390                   410
         .                     .                     .
GAATAAAAAACACGCTTTTTCAGTTCGAGTTTATCATTATCAATACTGCCATTTCAAAGA
       430                   450                   470
         .                     .                     .
ATACGTAAATAATTAATAGTAGTGATTTTCCTAACTTTATTTAGTCAAAAATTAGCCTTT
       490                   510                   530
         .                     .                     .
TAATTCTGCTGTAACCCGTACATGCCCAAAATAGGGGGCGGGTTACACAGAATATATAAC
       550                   570                   590
         .                     .                     .
ATCGTAGGTGTCTGGGTGAACAGTTTATCCCTGGCATCCACTAAATATAATGGAGCTCGC
       610                   630                   650
         .                     .                     .
TTTTAAGCTGGCATCCAGAAAAAAAAAGAATCCCAGCACCAAAATATTGTTTTCTTCACC
       670                   690                   710
         .                     .                     .
AACCATCAGTTCATAGGTCCATTCTCTTAGCGCAACTACAGAGAACAGGGGCACAAACAG
       730                   750                   770
         .                     .                     .
GCAAAAACGGGCACAACCTCAATGGAGTGATGCAACCTGCCTGGAGTAAATGATGACAC
       790                   810                   830
         .                     .                     .
AAGGCAATTGACCCACGCATGTATCTATCTCATTTTCTTACACCTTCTATTACCTTCTGC
```

FIG. 5A

```
                850                         870                         890
                 .                           .                           .
     TCTCTCTGATTTGGAAAAAGCTGAAAAAAAAGGTTGAAACCAGTTCCCTGAAATTATTCC
                910                         930                         950
                 .                           .                           .
     CCTACTTGACTAATAAGTATATAAAGACGGTAGGTATTGATTGTAATTCTGTAAATCTAT
                970                         990                        1010
                 .                           .                           .
     TTCTTAAACTTCTTAAATTCTACTTTTATAGTTAGTCTTTTTTTTAGTTTTAAAACACCA
               1030                        1050                        1070
                 .                           .                           .
     AGAACTTAGTTTCGAATAAACACACATAAACAAACAAAATGATGGCTCCCGATCCTAATG
                                                   MetMetAlaProAspProAsnA
               1090                        1110                        1130
                 .                           .                           .
     CAAATCCAAATGCAAACCCAAATGCAAACCCAAACGCAAACCCCAATGCAAATCCTAATG
     laAsnProAsnAlaAsnProAsnAlaAsnProAsnAlaAsnProAsnAlaAsnProAsnA
               1150                        1170                        1190
                 .                           .                           .
     CAAACCCCAATGCAAATCCTAATGCAAATCCTAATGCCAATCCAAATGCAAATCCAAATG
     laAsnProAsnAlaAsnProAsnAlaAsnProAsnAlaAsnProAsnAlaAsnProAsnA
               1210                        1230                        1250
                 .                           .                           .
     CAAACCCAAACGCAAACCCCAATGCAAATCCTAATGCCAATCCAAATGCAAATCCAAATG
     laAsnProAsnAlaAsnProAsnAlaAsnProAsnAlaAsnProAsnAlaAsnProAsnA
               1270                        1290                        1310
                 .                           .                           .
     CAAACCCAAATGCAAACCCAAATGCAAACCCCAATGCAAATCCTAATAAAAACAATCAAG
     laAsnProAsnAlaAsnProAsnAlaAsnProAsnAlaAsnProAsnLysAsnAsnGlnG
               1330                        1350                        1370
                 .                           .                           .
     GTAATGGACAAGGTCACAATATGCCAAATGACCCAAACCGAAATGTAGATGAAAATGCTA
     lyAsnGlyGlnGlyHisAsnMetProAsnAspProAsnArgAsnValAspGluAsnAlaA
               1390                        1410                        1430
                 .                           .                           .
     ATGCCAACAATGCTGTAAAAAATAATAATAACGAAGAACCAAGTGATAAGCACATAGAAC
     snAlaAsnAsnAlaValLysAsnAsnAsnAsnGluGluProSerAspLysHisIleGluG
               1450                        1470                        1490
                 .                           .                           .
     AATATTTAAAGAAAATAAAAAATTCTATTTCAACTGAATGGTCCCCATGTAGTGTAACTT
     lnTyrLeuLysLysIleLysAsnSerIleSerThrGluTrpSerProCysSerValThrC
```

FIG. 5B

```
           1510                1530                1550
             .                   .                   .
GTGGAAATGGTATTCAAGTTAGAATAAAGCCTGGCTCTGCTAATAAACCTAAAGACGAAT
ysGlyAsnGlyIleGlnValArgIleLysProGlySerAlaAsnLysProLysAspGluL
           1570                1590                1610
             .                   .                   .
TAGATTATGAAAATGATATTGAAAAAAAAATTTGTAAAATGGAAAAGTGCTCGAGTGTGT
euAspTyrGluAsnAspIleGluLysLysIleCysLysMetGluLysCysSerSerValP
           1630                1650                1670
             .                   .                   .
TTAATGTCGTAAATAGTCGACCTGTGACGAACATGGAGAACATCACATCAGGATTCCTAG
heAsnValValAsnSerArgProValThrAsnMetGluAsnIleThrSerGlyPheLeuG
           1690                1710                1730
             .                   .                   .
GACCCCTGCTCGTGTTACAGGCGGGGTTTTTCTTGTTGACAAGAATCCTCACAATACCGC
lyProLeuLeuValLeuGlnAlaGlyPhePheLeuLeuThrArgIleLeuThrIleProG
           1750                1770                1790
             .                   .                   .
AGAGTCTAGACTCGTGGTGGACTTCTCTCAATTTTCTAGGGGGATCACCCGTGTGTCTTG
lnSerLeuAspSerTrpTrpThrSerLeuAsnPheLeuGlyGlySerProValCysLeuG
           1810                1830                1850
             .                   .                   .
GCCAAAATTCGCAGTCCCCAACCTCCAATCACTCACCAACCTCCTGTCCTCCAATTTGTC
lyGlnAsnSerGlnSerProThrSerAsnHisSerProThrSerCysProProIleCysP
           1870                1890                1910
             .                   .                   .
CTGGTTATCGCTGGATGTGTCTGCGGCGTTTTATCATATTCCTCTTCATCCTGCTGCTAT
roGlyTyrArgTrpMetCysLeuArgArgPheIleIlePheLeuPheIleLeuLeuLeuC
           1930                1950                1970
             .                   .                   .
GCCTCATCTTCTTATTGGTTCTTCTGGATTATCAAGGTATGTTGCCCGTTTGTCCTCTAA
ysLeuIlePheLeuLeuValLeuLeuAspTyrGlnGlyMetLeuProValCysProLeuI
           1990                2010                2030
             .                   .                   .
TTCCAGGATCAACAACAACCAATACGGGACCATGCAAAACCTGCACGACTCCTGCTCAAG
leProGlySerThrThrThrAsnThrGlyProCysLysThrCysThrThrProAlaGlnG
           2050                2070                2090
             .                   .                   .
GCAACTCTATGTTTCCCTCATGTTGCTGTACAAAACCTACGGATGGAAATTGCACCTGTA
lyAsnSerMetPheProSerCysCysCysThrLysProThrAspGlyAsnCysThrCysI
           2110                2130                2150
```

FIG. 5C

```
TTCCCATCCCATCGTCCTGGGCTTTCGCAAAATACCTATGGGAGTGGGCCTCAGTCCGTT
leProIleProSerSerTrpAlaPheAlaLysTyrLeuTrpGluTrpAlaSerValArgP 2170                2190                2210
            .                   .                   .

TCTCTTGGCTCAGTTTACTAGTGCCATTTGTTCAGTGGTTCGTAGGGCTTTCCCCCACTG
heSerTrpLeuSerLeuLeuValProPheValGlnTrpPheValGlyLeuSerProThrV 2230                2250                2270
            .                   .                   .

TTTGGCTTTCAGCTATATGGATGATGTGGTATTGGGGGCCAAGTCTGTACAGCATCGTGA
alTrpLeuSerAlaIleTrpMetMetTrpTyrTrpGlyProSerLeuTyrSerIleValS 2290                2310                2330
            .                   .                   .

GTCCCTTTATACCGCTGTTACCAATTTTCTTTTGTCTCTGGGTATACATTTAACGAATTC
erProPheIleProLeuLeuProIlePhePheCysLeuTrpValTyrIleEnd 2350                2370                2390
            .                   .                   .

CAAGCTGAAACAATTCAAAGGTTTTCAAATCAATCAAGAACTTGTCTCTGTGGCTGATCC 2410                2430                2450
            .                   .                   .

AAACTACAAATTTATGCATTGTCTGCCAAGACATCAAGAAGAAGTTAGTGATGATGTCTT 2470                2490                2510
            .                   .                   .

TTATGGAGAGCATTCCATAGTCTTTGAAGAAGCAGAAAACAGATTATATGCAGCTATGTC 2530                2550                2570
            .                   .                   .

TGCCATTGATATCTTTGTTAATAATAAAGGTAATTTCAAGGACTTGAAATAATCCTTCTT 2590                2610                2630
            .                   .                   .

TCGTGTTCTTAATAACTAATATATAAATACAGATATAGATGCATGAATAATGATATACAT 2650                2670                2690
            .                   .                   .

TGATTATTTTGCAATGTCAATTAAAAAAAAAAAATGTTAGTAAAACTATGTTACATTCCA
```

FIG. 5D

```
            2710              2730              2750
             .    .     .      .    .     .      .    .     .
     AGCAAATAAAGCACTTGGTTAAACGAAATTAACGTTTTTAAGACAGCCAGACCGCGGTCT 2770              2790              2810
             .    .     .      .    .     .      .    .     .
     AAAAATTTAAATATACACTGCCAACAAATTCCTTCGAGTTGTCCAATTTCACCACTTTTA 2830              2850              2870
             .    .     .      .    .     .      .    .     .
     TATTTTCATCAACTTCAGCAGATTCAACCTTCTCACATAGAACATTGGAATAAACAGCCT 2890              2910              2930
             .    .     .      .    .     .      .    .     .
     TAACACCACTTTCAAGTTTGCACAGCGTAATATGAGGAATTTTGTTTTGACAACACAACC 2950              2970              2990
             .    .     .      .    .     .      .    .     .
     CTTTAATTTTCTCATTGTTTTCATCAATTATGCATCCATCTTTATCTTTAGACAGTTCCA 3010              3030              3050
             .    .     .      .    .     .      .    .     .
     CTACAATAGCAATAGTTTTTTCATCCCAACATAGTTTTTCGAGCCTAAAATTCAGTTTGT 3070              3090              3110
             .    .     .      .    .     .      .    .     .
     CGGTCGTTTTTACCTGCGTATTTTGGTTATTACCAGAGCCTTGTGCATTTTCTATGCGGT 3130              3150              3170
             .    .     .      .    .     .      .    .     .
     TGTTATTGTACTCCGTTATCTGGTCAGTGTATCTGTTACAATATGATTCCACAACTTTTT 3190              3210              3230
             .    .     .      .    .     .      .    .     .
     TGCCTCTTTTTCACGGGACGACATGACATGACCTAATGTTATATGAAGTTCCTTCTGAAC
```

FIG. 5E

```
           3250              3270              3290
             .        .        .        .        .        .
TTTTCCACTAGCTAGTAAATGCTTGAATTTCTCAGTCAGCTCTGCATCGCTAGCAATACA 3310              3330              3350
             .        .        .        .        .        .
CCTCTTGACCAATTCAATAATTTCATCGTAGTTTTCTATTTAGCTGAGATATATGTAGGT 3370              3390              3410
             .        .        .        .        .        .
TTAATTAACTTAGCGTTTTTTGTTGATTATTGTTGCCTTTACCAACTATTTTTCTCACAG 3430              3450              3470
             .        .        .        .        .        .
TAGGTTTGTAATCTAAGCTCCTTCTGAACGCTGTCTCAATTTCATCATCTTTCGGGATCT

3490
             .        .
CTGGTACCAAAATTGGATAAGCTT
```

FIG. 5F

| | | | | | | | | | | | | | |
|---|---|---|---|---|---|---|---|---|---|---|---|---|---|
|Met|Met|Ala|Pro|Asp|Pro|Asn|Ala|Asn|Pro|Asn|Ala|Asn|Pro|Asn|Ala|

Met Met Ala Pro Asp Pro Asn Ala Asn Pro Asn Ala Asn Pro Asn Ala
1       5             10              15

Asn Pro Asn Ala Asn Pro Asn Ala Asn Pro Asn Ala Asn Pro Asn Ala
            20              25              30

Asn Pro Asn Ala Asn Pro Asn Ala Asn Pro Asn Ala Asn Pro Asn Ala
        35              40              45

Asn Pro Asn Ala Asn Pro Asn Ala Asn Pro Asn Ala Asn Pro Asn Ala
        50              55              60

Asn Pro Asn Ala Asn Pro Asn Ala Asn Pro Asn Ala Asn Pro Asn Lys
65              70              75              80

Asn Asn Gln Gly Asn Gly Gln Gly His Asn Met Pro Asn Asp Pro Asn
                85              90              95

Arg Asn Val Asp Glu Asn Ala Asn Ala Asn Ser Ala Val Lys Asn Asn
            100             105             110

Asn Asn Glu Glu Pro Ser Asp Lys His Ile Lys Glu Tyr Leu Asn Lys
        115             120             125

Ile Gln Asn Ser Leu Ser Thr Glu Trp Ser Pro Cys Ser Val Thr Cys
    130             135             140

Gly Asn Gly Ile Gln Val Arg Ile Lys Pro Gly Ser Ala Asn Lys Pro
145             150             155             160

Lys Asp Glu Leu Asp Tyr Ala Asn Asp Ile Glu Lys Lys Ile Cys Lys
                165             170             175

Met Glu Lys Cys Ser Ser Val Phe Asn Val Val Asn Ser Ser Ile Gly
            180             185             190

Leu Gly Pro Val Thr Asn Met Glu Asn Ile Thr Ser Gly Phe Leu Gly

FIG. 9A

```
                   195                        200                        205
    Pro Leu Leu Val Leu Gln Ala Gly Phe Phe Leu Leu Thr Arg Ile Leu
            210                 215                     220

Thr Ile Pro Gln Ser Leu Asp Ser Trp Trp Thr Ser Leu Asn Phe Leu
    225                 230                 235                     240

Gly Gly Ser Pro Val Cys Leu Gly Gln Asn Ser Gln Ser Pro Thr Ser
                    245                 250                 255

Asn His Ser Pro Thr Ser Cys Pro Pro Ile Cys Pro Gly Tyr Arg Trp
                    260                 265                 270

Met Cys Leu Arg Arg Phe Ile Ile Phe Leu Phe Ile Leu Leu Leu Cys
            275                 280                 285

Leu Ile Phe Leu Leu Val Leu Leu Asp Tyr Gln Gly Met Leu Pro Val
            290                 295                 300

Cys Pro Leu Ile Pro Gly Ser Thr Thr Thr Asn Thr Gly Pro Cys Lys
    305                 310                 315                     320

Thr Cys Thr Thr Pro Ala Gln Gly Asn Ser Met Phe Pro Ser Cys Cys
                    325                 330                 335

Cys Thr Lys Pro Thr Asp Gly Asn Cys Thr Cys Ile Pro Ile Pro Ser
                    340                 345                 350

Ser Trp Ala Phe Ala Lys Tyr Leu Trp Glu Trp Ala Ser Val Arg Phe
            355                 360                 365

Ser Trp Leu Ser Leu Leu Val Pro Phe Val Gln Trp Phe Val Gly Leu
            370                 375                 380

Ser Pro Thr Val Trp Leu Ser Ala Ile Trv Met Met Trp Tyr Trp Gly
    385                 390                 395                     400

Pro Ser Leu Tyr Ser Ile Val Ser Pro Phe Ile Pro Leu Leu Pro Ile
                    405                 410                     415
```

FIG. 9B

```
Phe Phe Cys Leu Trp Val Tyr Ile
            420

AAGCTTACCA GTTCTCACAC GGAACACCAC TAATGGACAC AAATTCGAAA TACTTTGACC
60

CTATTTTCGA GGACCTTGTC ACCTTGAGCC CAAGAGAGCC AAGATTTAAA TTTTCCTATG
120

ACTTGATGCA AATTCCCAAA GCTAATAACA TGCAAGACAC GTACGGTCAA GAAGACATAT
180

TTGACCTCTT AACTGGTTCA GACGCGACTG CCTCATCAGT AAGACCCGTT GAAAAGAACT
240

TACCTGAAAA AAACGAATAT ATACTAGCGT TGAATGTTAG CGTCAACAAC AAGAAGTTTA
300

ATGACGCGGA GGCCAAGGCA AAAAGATTCC TTGATTACGT AAGGGAGTTA GAATCATTTT
360

GAATAAAAAA CACGCTTTTT CAGTTCGAGT TTATCATTAT CAATACTGCC ATTTCAAAGA
420

ATACGTAAAT AATTAATAGT AGTGATTTTC CTAACTTTAT TTAGTCAAAA ATTAGCCTTT
480

TAATTCTGCT GTAACCCGTA CATGCCCAAA ATAGGGGGCG GGTTACACAG AATATATAAC
540

ATCGTAGGTG TCTGGGTGAA CAGTTTATCC CTGGCATCCA CTAAATATAA TGGAGCTCGC
600

TTTTAAGCTG GCATCCAGAA AAAAAAAGAA TCCCAGCACC AAAATATTGT TTTCTTCACC
660
```

FIG. 9C

```
AACCATCAGT  TCATAGGTCC  ATTCTCTTAG  CGCAACTACA  GAGAACAGGG  GCACAAACAG
720

GCAAAAAACG  GGCACAACCT  CAATGGAGTG  ATGCAACCTG  CCTGGAGTAA  ATGATGACAC
780

AAGGCAATTG  ACCCACGCAT  GTATCTATCT  CATTTTCTTA  CACCTTCTAT  TACCTTCTGC
840

TCTCTCTGAT  TTGGAAAAAG  CTGAAAAAAA  AGGTTGAAAC  CAGTTCCCTG  AAATTATTCC
900

CCTACTTGAC  TAATAAGTAT  ATAAAGACGG  TAGGTATTGA  TTGTAATTCT  GTAAATCTAT
960

TTCTTAAACT  TCTTAAATTC  TACTTTTATA  GTTAGTCTTT  TTTTTAGTTT  TAAAACACCA
1020

AGAACTTAGT  TTCGAATAAA  CACACATAAA  CAAACAAAAT  GATGGCTCCC  GATCCTAATG
1080

CAAATCCAAA  TGCAAACCCA  AACGCAAACC  CCAATGCAAA  TCCTAATGCA  AACCCCAATG
1140

CAAATCCTAA  TGCAAATCCT  AATGCCAATC  CAAATGCAAA  TCCAAATGCA  AACCCAAACG
1200

CAAACCCCAA  TGCAAATCCT  AATGCCAATC  CAAATGCAAA  TCCAAATGCA  AACCCAAATG
1260

CAAACCCAAA  TGCAAACCCC  AATGCAAATC  CTAATAAAAA  CAATCAAGGT  AATGGACAAG
1320

GTCACAATAT  GCCAAATGAC  CCAAACCGAA  ATGTAGATGA  AAATGCTAAT  GCCAACAGTG
1380

CTGTAAAAAA  TAATAATAAC  GAAGAACCAA  GTGATAAGCA  CATAAAAGAA  TATTTAAACA
1440
```

FIG. 9D

```
AAATACAAAA TTCTCTTTCA ACTGAATGGT CCCCATGTAG TGTAACTTGT GGAAATGGTA
1500

TTCAAGTTAG AATAAAGCCT GGCTCTGCTA ATAAACCTAA AGACGAATTA GATTATGCAA
1560

ATGATATTGA AAAAAAAATT TGTAAAATGG AAAAATGTTC CAGTGTGTTT AATGTCGTAA
1620

ATAGTTCAAT AGGATTAGGG CCTGTGACGA ACATGGAGAA CATCACATCA GGATTCCTAG
1680

GACCCCTGCT CGTGTTACAG GCGGGGTTTT TCTTGTTGAC AAGAATCCTC ACAATACCGC
1740

AGAGTCTAGA CTCGTGGTGG ACTTCTCTCA ATTTTCTAGG GGGATCACCC GTGTGTCTTG
1800

GCCAAAATTC GCAGTCCCCA ACCTCCAATC ACTCACCAAC CTCCTGTCCT CCAATTTGTC
1860

CTGGTTATCG CTGGATGTGT CTGCGGCGTT TTATCATATT CCTCTTCATC CTGCTGCTAT
1920

GCCTCATCTT CTTATTGGTT CTTCTGGATT ATCAAGGTAT GTTGCCCGTT TGTCCTCTAA
1980

TTCCAGGATC AACAACAACC AATACGGGAC CATGCAAAAC CTGCACGACT CCTGCTCAAG
2040

GCAACTCTAT GTTTCCCTCA TGTTGCTGTA CAAAACCTAC GGATGGAAAT TGCACCTGTA
2100

TTCCCATCCC ATCGTCCTGG GCTTTCGCAA ATACCTATG GGAGTGGGCC TCAGTCCGTT
2160

TCTCTTGGCT CAGTTTACTA GTGCCATTTG TTCAGTGGTT CGTAGGGCTT TCCCCCACTG
2220
```

FIG. 9E

```
TTTGGCTTTC AGCTATATGG ATGATGTGGT ATTGGGGGCC AAGTCTGTAC AGCATCGTGA
2280

GTCCCTTTAT ACCGCTGTTA CCAATTTTCT TTTGTCTCTG GGTATACATT TAACGAATTC
2340

CAAGCTGAAA CAATTCAAAG GTTTTCAAAT CAATCAAGAA CTTGTCTCTG TGGCTGATCC
2400

AAACTACAAA TTTATGCATT GTCTGCCAAG ACATCAAGAA GAAGTTAGTG ATGATGTCTT
2460

TTATGGAGAG CATTCCATAG TCTTTGAAGA AGCAGAAAAC AGATTATATG CAGCTATGTC
2520

TGCCATTGAT ATCTTTGTTA ATAATAAAGG TAATTTCAAG GACTTGAAAT AATCCTTCTT
2580

TCGTGTTCTT AATAACTAAT ATATAAATAC AGATATAGAT GCATGAATAA TGATATACAT
2640

TGATTATTTT GCAATGTCAA TTAAAAAAAA AAAATGTTAG TAAAACTATG TTACATTCCA
2700

AGCAAATAAA GCACTTGGTT AAACGAAATT AACGTTTTTA AGACAGCCAG ACCGCGGTCT
2760

AAAAATTTAA ATATACACTG CCAACAAATT CCTTCGAGTT GTCCAATTTC ACCACTTTTA
2820

TATTTTCATC AACTTCAGCA GATTCAACCT TCTCACATAG AACATTGGAA TAAACAGCCT
2880

TAACACCACT TTCAAGTTTG CACAGCGTAA TATGAGGAAT TTTGTTTTGA CAACACAACC
2940

CTTTAATTTT CTCATTGTTT TCATCAATTA TGCATCCATC TTTATCTTTA GACAGTTCCA
3000
```

FIG. 9F

```
CTACAATAGC AATAGTTTTT TCATCCCAAC ATAGTTTTTC GAGCCTAAAA TTCAGTTTGT
3060

CGGTCGTTTT TACCTGCGTA TTTTGGTTAT TACCAGAGCC TTGTGCATTT TCTATGCGGT
3120

TGTTATTGTA CTCCGTTATC TGGTCAGTGT ATCTGTTACA ATATGATTCC ACAACTTTTT
3180

TGCCTCTTTT TCACGGGACG ACATGACATG ACCTAATGTT ATATGAAGTT CCTTCTGAAC
3240

TTTTCCACTA GCTAGTAAAT GCTTGAATTT CTCAGTCAGC TCTGCATCGC TAGCAATACA
3300

CCTCTTGACC AATTCAATAA TTTCATCGTA GTTTTCTATT TAGCTGAGAT ATATGTAGGT
3360

TTAATTAACT TAGCGTTTTT TGTTGATTAT TGTTGCCTTT ACCAACTATT TTTCTCACAG
3420

TAGGTTTGTA ATCTAAGCTC CTTCTGAACG CTGTCTCAAT TTCATCATCT TTCGGGATCT
3480

CTGGTACCAA AATTGGATAA GCTT
3504
```

FIG. 9G

HYBRID PROTEIN BETWEEN CS FROM PLASMODIUM AND HBSAG

This is a continuation of application Ser. No. 08/442,612, filed May 17, 1995, now abandoned, which is a continuation of application Ser. No. 08/244,085, filed Oct. 21, 1994, now abandoned, which is a 371 of PCT/EP92/02591, filed Nov. 11, 1992, which is a continuation-in-part of Ser. No. 07/842,694, filed Feb. 27, 1992, now abandoned.

Malaria, is one of the world's major health problems with 2 to 4 million people dying from the disease each year. One of the most acute forms of the disease is caused by the protozoan parasite, *Plasmodium falciparum* which is responsible for most of the mortality attributable to Malaria.

The life cycle of *P. falciparum* is complex, requiring two hosts, man and mosquito for completion. The infection of man is initiated by the inoculation of sporozoites in the saliva of an infected mosquito. The sporozoites migrate to the liver and there infect hepatocytes where they differentiate, via the exoerythrocytic intracellular stage, into the merozoite stage which infects red blood cells (RBC) to initiate cyclical replication in the asexual blood stage. The cycle is completed by the differentiation of a number of merozoites in the RBC into sexual stage gametocytes which are ingested by the mosquito, where they develop through a series of stages in the midgut to produce sporozoites which migrate to the salivary gland.

The sporozoite stage of *P. falciparum* has been identified as a potential target of a malaria vaccine. The major surface protein of the sporozoite is known as circumsporozoite protein (CS Protein). This protein from strain 7G8 has been cloned, expressed and sequenced (Dame et al Science 225 (1984) p593). The protein from strain 7G8 is characterised by having a central immunodominant repeat region comprising a tetrapeptide Asn-Ala-Asn-Pro repeated 37 times but interspersed with four minor repeats Asn-Val-Asp-Pro. In other strains the number of major and minor repeats vary as well as their relative position. This central portion is flanked by an N and C terminal portion composed of non-repetitive amino acid sequences designated as the repeatless portion of the CS protein.

It has been shown that irradiated sporozoites can provide significant protection against experimental human malaria (Am. J. Trop. Med. Hyg. 24: 297–402, 1975). However, production difficulties makes the use of irradiated sporozoite impractical from the point of view of producing a vaccine.

Several groups have proposed subunit vaccines based on the circumsporozoite protein. Two of these vaccines have undergone clinical testing; one is a synthetic peptide, the other is a recombinant protein (Ballou et al Lancet: i 1277 (1987) and Herrington et al Nature 328:257 (1987).

These vaccines were successful in stimulating an anti-sporozoite response. Nonetheless, the magnitude of the response was disappointing, with some vaccinees not making a response at all. Furthermore, the absence of "boosting" of antibody levels on subsequent injections and results of in vitro lymphocyte proliferation assays suggested that T-cells of most of these volunteers did not recognise the immunodominant repeat. Nonetheless, one vaccinee in each study did not develop parasitemia.

BRIEF DESCRIPTION OF THE FIGURES

FIG. 5 is the nucleotide sequence of the RTS expression cassette and predicted translation product of the RTS-HBsAg hybrid protein. The translation product initiated from the TDH3 ATG codon is shown below the DNA sequence.

FIG. 9 is the nucleotide sequence of the RTS* expression cassette and predicted translation product of the hybrid protein.

Figure 1A:
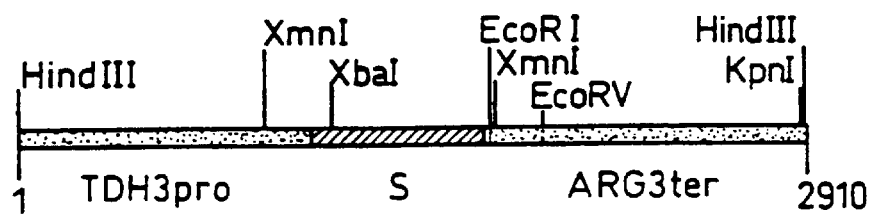
FIG. 1 is a restriction endonuclease map of (A) the S expression cassette and (B) the RTS expression cassette. The extent of each coding sequence is indicated by the black bar.

The present invention provides a new, improved antigen for use in malaria vaccines which not only produces a humoral response, but also a cellular immune response. Preferably the antigen induces the production of neutralising antibodies against the immunodominant repeat. Most preferably, the antigen should also elicit effector T cell mediated immune responses of the $CD4^+$ and $CD8^+$ cytotoxic T lymphocyte (CTL) type and of the delayed type hypersensitivity type and also, preferably be able to induce T helper (TH) memory cells.

Accordingly, the present invention provides a hybrid protein comprising substantially all the C-terminal portion of the CS protein, four or more tandem repeats of the immunodominant region, and the Surface antigen from Hepatitis B virus (HBsAg). Preferably the hybrid protein comprises a sequence which contains at least 160 amino acids which is substantially homologous to the C-terminal portion of the CS protein. The CS protein may be devoid of the last 12 amino-acids from the C terminal.

In particular there is provided a protein which comprises a portion of the CS protein of *P. falciparum* substantially as corresponding to amino acids 210–398 of *P. falciparum* 7G8 fused in frame via a linear linker to the N-terminal of HBsAg. The linker may comprise a portion of preS2 from HBsAg.

The present invention also provides DNA sequences encoding the proteins of the present invention.

A particularly preferred embodiment is the hybrid protein designated RTS. The amino acid sequence of RTS is shown in FIG. 5. This hybrid consists of:

A methionine-residue, encoded by nucleotides 1059 to 1061, derived from the *Sacchromyes cerevisiae* TDH3 gene sequence. (Musti A. M. et al Gene 1983 25 133–143.

Three amino acids, Met Ala Pro, derived from a nucleotide sequence (1062 to 1070) created by the cloning procedure used to construct the hybrid gene.

C A stretch of 189 amino acids, encoded by nucleotides 1071 to 1637 representing amino acids 210 to 398 of the circumsporozoite protein (CSP) of *Plasmodium falciparum* strain 7G8 (Dame et al supra).

An amino acid (Arg) encoded by nucleotides 1638 to 1640, created by the cloning procedure used to construct the hybrid gene.

Four amino acids, Pro Val Thr Asn, encoded by nucleotides 1641 to 1652, and representing the four carboxy terminal residues of the hepatitis B virus (adw serotype) preS2 protein (9).

A stretch of 226 amino acids, encoded by nucleotides 1653 to 2330, and specifying the S protein of hepatitis B virus (adw serotype).

In an alternative embodiment there is provided a hybrid protein designated RTS* which was generated using the CSP gene sequence from *P. falciparum* NF54 (Mol. Biochem Parisitol. 35: 185–190, 1989) and comprises substantially all of the region 207 to 395 of the CS protein from *P falciparum* NF54.

In particular RTS* comprises:

A Methionine, encoded by nucleotides 1059 to 1061, derived from the TDH3 gene sequence.

Three amino acids, Met Ala Pro, derived from a nucleotide sequence (1062 to 1070) created by the cloning procedure used to construct the hybrid gene.

A stretch of 189 amino acids, encoded by nucleotides 1071 to 1637 representing amino acids 207 to 395 of the circumsporozoite protein (CSP) of *Plasmodium falciparum* strain NF54 (Mol.Biochem.Parasitol, 35:185–190, 1989).

An amino acid (Gly) encoded by nucleotides 1638 to 1640, created by the cloning procedure used to construct the hybrid gene.

Four amino acids, Pro Val Thr Asn, encoded by nucleotides 1641 to 1652, and representing the four carboxy terminal residues of the hepatitis B virus (adw serotype) preS2 protein (Nature 280:815–819, 1979).

A stretch of 226 amino acids, encoded by nucleotides 1653 to 2330, and specifying the S protein of hepatitis B virus (adw serotype) (Nature 280:815–819, 1979).

The amino acid sequence of RTS* is depicted in FIG. 9.

An expression cassette containing RTS* was constructed and comprises the following features:

A promoter sequence, extending from nucleotide 1 through 1058, derived from the *S. cerevisiae* TDH3 gene.

An open reading frame starting at nucleotide 1059 and extending to nucleotide 2330. This open reading frame is immediately followed by a translational stop codon, TAA (nucleotides 2331 to 2333). The open reading frame encodes the amino acids specifying the hybrid RTS* protein.

A transcription termination sequence contained within the sequence extending from base pair 2334 to 3504, derived from the *S. cerevisiae* ARG3 gene.

The nucleotide sequence is depicted in FIG. 10.

The DNA sequences encoding the proteins of the present invention are, in a preferred embodiment flanked by transcriptional control elements, preferably derived from yeast genes and incorporated into an expression vector.

Such vectors are a further aspect of the invention. A preferred promoter is the promoter from the *S. cerevisiae* TDH3 gene Musti et al supra).

The invention also relates to a host cell transformed with a vector according to the invention. Host cells can be prokaryotic or eukaryotic but preferably, are yeast, such as *S. cerevisiae*. In such a host, the hybrid protein, for example RTS will be expressed as lipoprotein particle. The chosen recipient yeast strain preferably already carries in its genome several integrated copies of an hepatitis B S expression cassette. The resulting strain synthesizes two polypeptides, S and RTS (or other hybrid protein of the invention), that spontaneously co-assemble into mixed (for example RTS, S or RTS*, S) lipoprotein particles. These particles, advantageously present the CSP sequences of the hybrid at their surface. These mixed particles also form part of the present invention. Advantageously the ratio or RTS:S or RTS*:S in these mixed particles is 1:4.

The present invention also relates to vaccines comprising an immunoprotective amount of a protein or particle according to the invention in admixture with a suitable diluent or carrier.

In the vaccine of the invention, an aqueous solution of the hybrid may be used directly. Alternatively, the protein with or without prior lyophilisation can be mixed or absorbed with any of the known adjuvants which include but are not limited to alum, muramyl dipeptide, saponins such as Quil A.

An immunostimulant may alternatively or in addition be included. In a preferred embodiment this immunostimulant will be 3 Deacylated monophosphoryl lipid A (3D-MPL).

3 Deacylated monophosphoryl lipid A is known from U.S. Pat. No. 4,912,094 and UK patent application No. 2,220,211 (Ribi) and is available from Ribi Immunochem, Montana, U.S.A.

The protein of the present invention may also be encapsulated into microparticles such as liposomes.

Vaccine preparation is generally described in New Trends and Developments in Vaccines, edited by Voller et al., University Park Press, Baltimore, Md., U.S.A., 1978. Encapsulation within liposomes is described, for example, by Fullerton, U.S. Pat. No. 4,235,877.

Conventional adjuvants may be used, but a preferred immunostimulant is 3-deacylated monophosphoryl lipid A (3D-MPL).

Typically when 3D-ML is used the antigen and 3D-MPL are delivered with alum or presented in an oil in water emulsion or multiple oil in water emulsions. The incorporation of 3D-MPL is advantageous since it is a stimulator of effector T-cells responses.

Accordingly a preferred embodiment of the present invention provides a vaccine comprising a hybrid protein as herein described, preferably RTS, or RTS* in combination with 3D-MPL and a carrier. Typically the carrier will be an oil in water emulsion or alum.

In a most preferred embodiment the hybrid protein is presented as a particle or mixed particle as herein described.

The amount of the protein of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally it is expected that each does will comprise 1–1000 μg of protein, preferably 1–200 μg most preferably 10–100 μg. An optimal amount for a particular vaccine can be ascertained by standard studies involving observation of antibody titres and other responses in subjects. Following an initial vaccination, subjects will preferably receive a boost in about 4 weeks, followed by repeated boosts every six months for as long as a risk of infection exists. The immune response to the protein of this invention is enhanced by the use of adjuvant and or an immuno stimulant.

The proteins of the present invention are preferably expressed in yeast, and especially those belonging to the genus Saccharomyces.

A further aspect of the present invention is to provide a process for the preparation of hybrid protein of the invention, which process comprises expressing DNA sequence encoding the protein, in a suitable host, preferably a yeast, and recovering the product.

It is particularly preferred to express the protein of the invention in a Sacchromyces strain. When RTS, for example is expressed in such strains it spontaneously assembles into multimeric lipoprotein particles.

These particles are highly immunogenic and induce a strong humoral response, as well as immunological memory and also are capable of inducing effector T cells of the CTL and DTH types.

A further aspect of the invention lies in a method of treating a patient susceptible to plasmodium infections by administering an effective amount of a vaccine as hereinbefore described.

EXAMPLE 1

1. Construction of the RTS.S strain RIT4383

The S. cerevisiae strain, RIT4383 used for production of particles containing both the S and RTS polypeptides, carries separate expression cassettes for each protein. The S gene expression cassette has been integrated in 5 to 6 copies at least two sites in genome using a linear integration vector with homology to resident Ty retrotransponsons. The RTS gene expression cassette has been integrated in 2 to 3 copies at one or 2 sites in the genome, using a linear integration vector similar to the one employed for the integration of the S gene cassette. Expression from both types of cassette is driven by a promoter derived from the yeast TDH3 gene.

1.1 Construction of the S Expression cassette and Integrative Vector (pRIT13034)

The S gene expression cassette (FIG. 1A) identical to that found in strain RIT4376 (1) and consists of a 1058 bp TDH3 promoter fragment, 681 bp of S gene sequence, a 6 bp spacer containing an EcoRI linker and a 1165 bp fragment carrying the Arg3 transcription terminator. The S coding sequence was derived by subcloning from a complete genomic clone (pRIT10616) of a virus of (adw serotype).

Figure 2A:
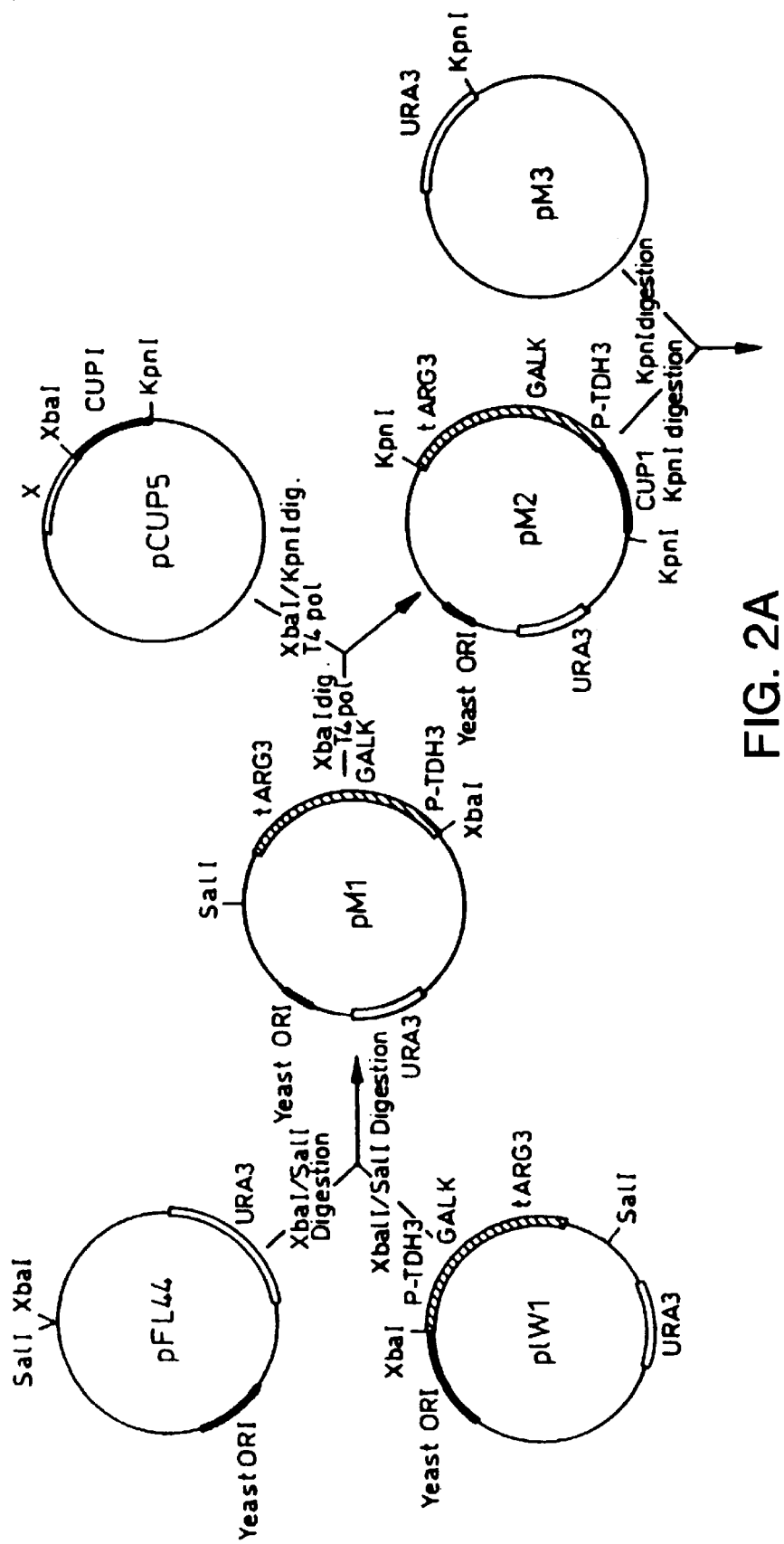
FIG. 2 shows the construction of plasmid pRIT13034. Digestion with XhoI endonuclease liberates a 8.5 Kb linear DNA fragment carrying the S expression cassette for integration into the yeast chromosome by homology of the free ends with resident Ty elements.
Figure 2B:
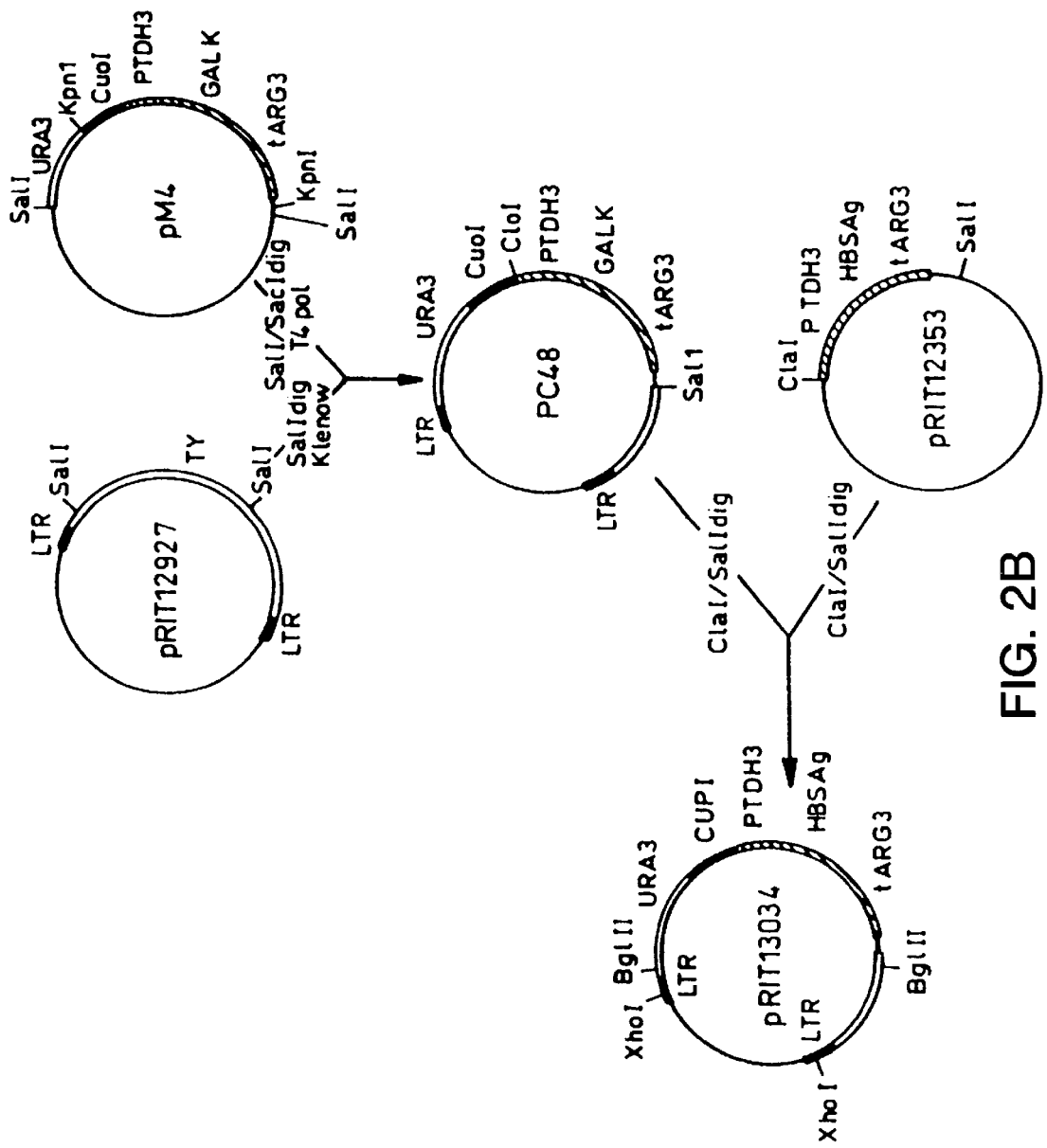
Figure 3:
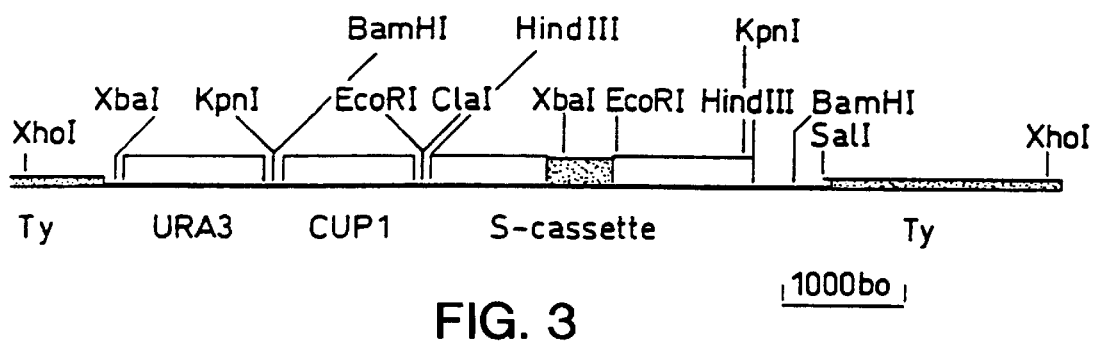
FIG. 3 is a restriction map of the 8.5 Kb linear XhoI fragment from pRIT13034. The linear fragment contains the URA3 and CUP1 genes for selection of transformed yeast cells together with the S expression cassette.

The structure of the Ty vector, pRIT13034, used for integration of the S expression cassette into the yeast genome, is shown in FIG. 2. The construction and use of this type of vector for integration of expression cassettes in the yeast genome is described in Jacobs et al. (2). pRIT13034 contains the S gene cassette, the URA3 gene and the CUP1 gene inserted within a copy of a Ty element cloned on pUC9. The URA3 gene and the CUP1 gene both provide selectable markers that allow to distinguish transformed yeast colonies from untransformed colonies. pUC9 is described by Vieira & Messing (3), the URA3 fragment is from pFL44 (F. Lacroute, CNRS, Strasbourg), the CUP1 fragment is from pCUP5 (T. Butt, SKF Labs, Philadelphia), the Ty element is from Juniaux et al. (4) and the S gene cassette from pRIT12353. Digestion of pRIT13034 with XhoI endonuclease liberates the 8500 bp linear fragment shown in FIG. 3 which can integrate into the genome by homologous recombination of the free ends with resident Ty elements.

EXAMPLE 2

2. Construction of Strain Y1295

The recipient strain, EJ cup1D-3d (trp1, leu2, ura3, cup1, gal1D, MATα) was used for initial introduction by transformation of the linear vector fragment from pRIT13034. This strain contains a single disrupted cup1 locus, cup1.

After transformation with the linear XhoI fragment, Ura$^+$ colonies were isolated and screened for copper resistance. The more resistant transformants had integrated two to five copies of the vector as determined by Southern blotting analysis. Two transformant colonies copies were retained, MS9 with an estimated 3 to 4 copies and MS23 with 4 to 5 copies of the integrated linear vector. Strain MS23 was then crossed with strain EJ cup1D-7b (trp1, ura3, cup1, gal1D, MATα) and a haploid ascospore recovered to give strain MS23-2a.

This strain was then backcrossed to MS9 and a Leu$^-$, Trp$^-$ haploid segregant obtained (MS54-2c) containing 5 to 6 copies of the integrated expression cassette. Southern blotting showed that MS54-2C contained 4 to 5 tandem copies of the integration vector at one locus and a further single copy integrated at a different locus. All 5 to 6 copies of the expression cassette were intact as digestion of total yeast cell DNA with HindIII endonuclease to liberate the cassette fragment and Southern blotting with an S gene specific probe gave a single 3 kb band as expected. A spontaneous Trp$^+$ revertant of this strain was obtained, MS54-2c-T, and given the laboratory accesssion number Y1295.

EXAMPLE 3

CONSTRUCTION OF THE RTS-EXPRESSION CASSETTE

Figure 1B:
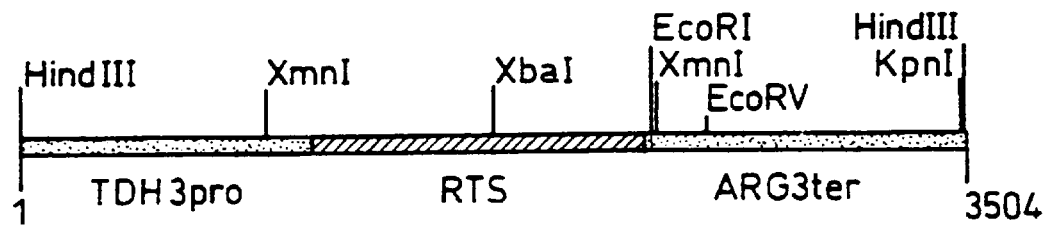
Figure 4:
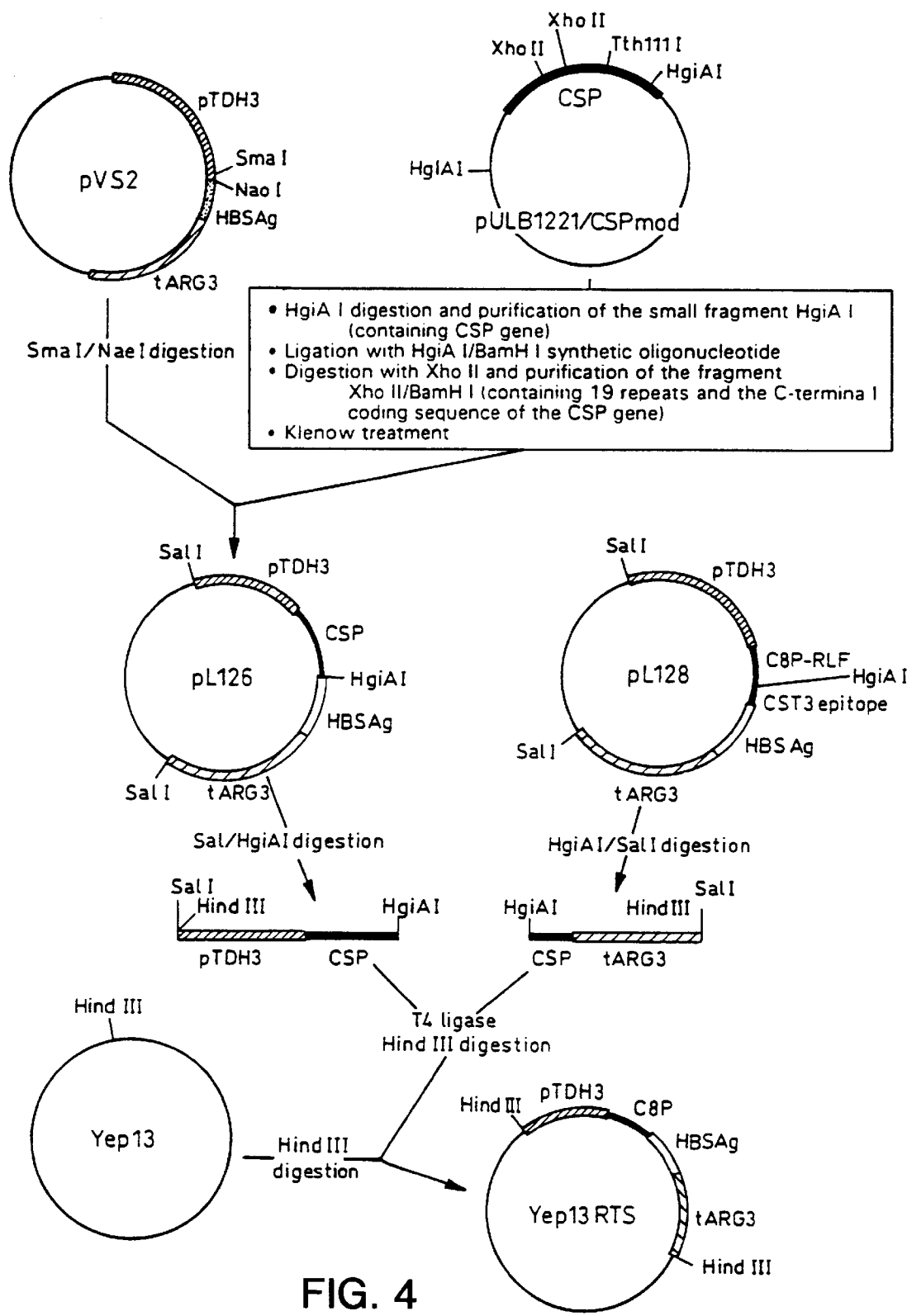
FIG. 4 shows the construction of the RTS expression cassette and its cloning in plasmid Yep13.

The expression cassette for the RTS hybrid protein was constructed by a multistep cloning procedure and was cloned in the E. coli yeast shuttle vector Yep13(6) yielding a plasmid Yep13RTS (FIG. 4). The structure of the cassette is shown in FIG. 1B. Its entire nucleotide sequence was determined either by direct sequencing (as for the coding sequence and parts of the flanking control sequences) or by consultation of the relevant literature (as for parts of the promotor and terminator sequences). The DNA sequence is illustrated in FIG. 5. It contains the following elements:

A promotor sequence, extending from nucleotide 1 through 1058, derived from the S. cerevisiae TDH3 gene.

An open reading frame starting at nucleotide 1059 and extending to nucleotide 2330. This open reading frame is immediately followed by a translational stop codon, TAA (nucleotides 2331 to 2333). The open reading frame encodes the amino acids specifying the hydrid RTS protein.

A transcription termination sequence contained within the sequence extending from base pair 2334 to 3504, derived from the S. cerevisiae ARG3 gene (Crabeel et al EMBO J. 1983 2: 205–212).

The amino acid sequence of the hybrid RTS protein, encoded by nucleotides 1059 to 2330 is indicated in FIG. 5 and contains the following elements:

A methionine-residue, encoded by nucleotides 1059 to 1061, derived from the TDH3 gene sequence.

Three amino acids, Met Ala Pro, derived from a nucleotide sequence (1062 to 1070) created by the cloning procedure used to construct the hybrid gene.

A stretch of 189 amino acids, encoded by nucleotides 1071 to 1637 representing amino acids 210 to 398 of the circumsporozoite protein (CSP) of Plasmodium falciparum strain 7G8 (8).

An amino acid (Arg) encoded by nucleotides 1638 to 1640, created by the cloning procedure used to construct the hybrid gene Four amino acids, Pro Val Thr Asn, encoded by nucleotides 1641 to 1652, and representing the four carboxy terminal residues of the hepatitis B virus (adw serotype) preS2 protein (9).

A stretch of 226 amino acids, encoded by nucleotides 1653 to 2330, and specifying the S protein of hepatitis B virus (adw serotype).

EXAMPLE 4

CONSTRUCTION OF THE RTS CASSETTE INTEGRATIVE VECTOR pRIT13539

Figure 6:
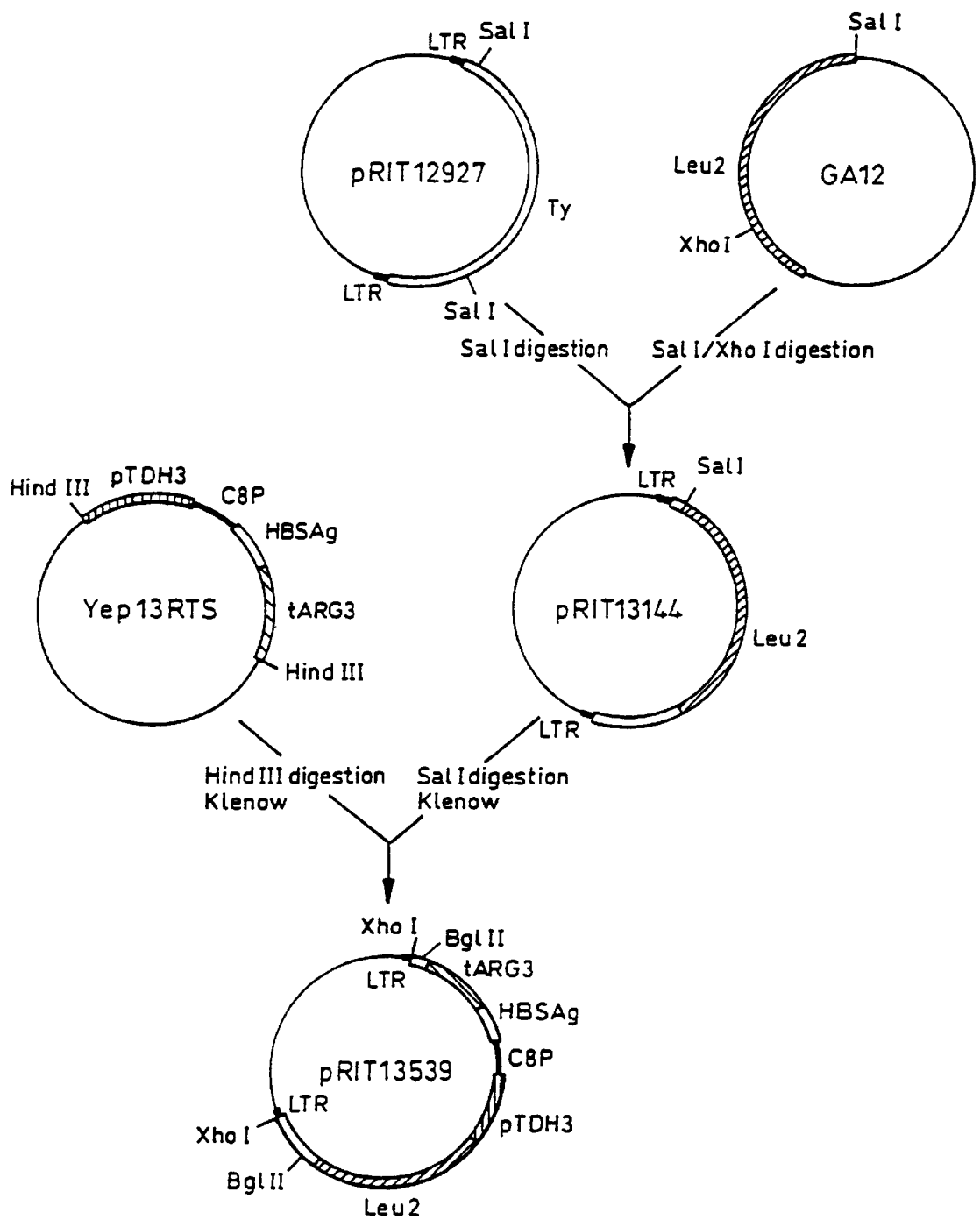
FIG. 6 shows the construction of plasmid pRIT13539. Digestion with BglII endonuclease liberates a 6.8 Kb linear DNA fragment carrying the RTS expression cassette for integration into the yeast chromosome by homology of the free ends with resident Ty elements.

The Construction of the RTS Cassette integrative vector pRIT13539 is shown on FIG. 6.

Figure 7:
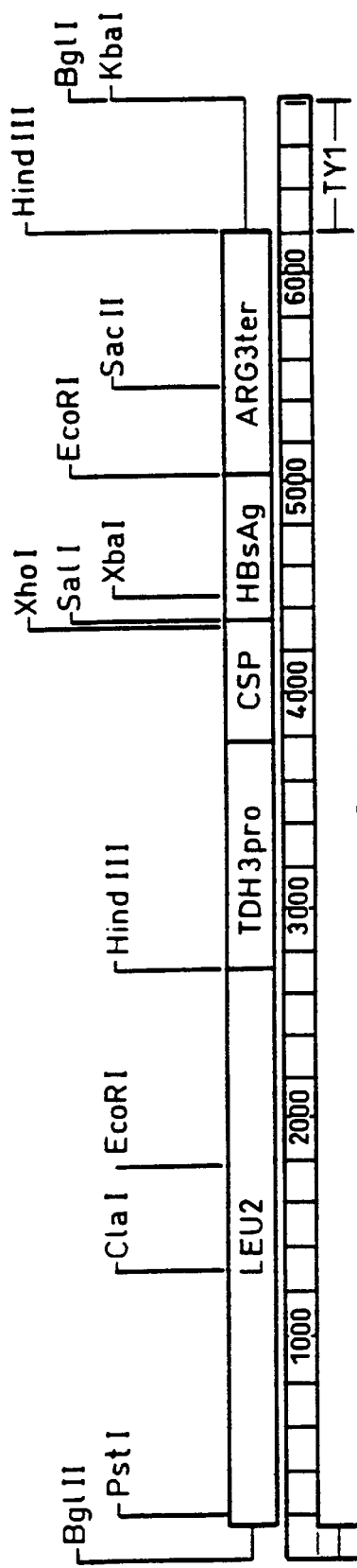
FIG. 7 is a restriction map of the 6.8 Kb linear BglII fragment from pRIT13539. The linear fragment contains the LEU2 gene for selection of transformed yeast cells together with the RTS expression cassette.

The RTS expression cassette was inserted on the Ty based integrative vector pRIT13144. This vector is a derivative of pRIT12927 (2) in which the LEU2 gene was inserted in the SalI site of the Ty element as a SalI-XhoI fragment isolated from the vector pCV9 (7). Thus, after insertion of the RTS expression cassette into pRIT13144, the resulting plasmid, pRIT13539, contains, in addition to the expression cassette, the yeast LEU2 gene as selective marker (FIG. 5). Digestion of pRIT13539 with BglII endonuclease liberates a 6.800 bp linear fragment shown in FIG. 7 which can integrate into the genome by homologous recombination of the free ends with resident Ty elements.

EXAMPLE 5

TRANSFORMATION OF STRAIN Y1295 AND GENERATION OF STRAIN RIT4383 (Y1530)

To obtain a strain expressing both S and RTS proteins, Y1295 was transformed with the 6800 bp linear BglII fragment (FIG. 7) with selection for Leu+ colonies. Several integrants containing sets of both expression cassettes present in the genome at various ratio were obtained. One selected transformant, expressing the RTS and S protein in a ratio of approximately 1:4 was given the official designation RIT4383 (the laboratory accession number is Y1530).

EXAMPLE 5b

TRANSFORMATION OF STRAIN Y1295 AND GENERATION OF STRAIN Y1631

A similar (to RTS) construct was generated using the CSP gene sequence derived from *P. falciparum* strain NF54 (Mol.Biochem.Parasitol.35:185–190, 1989). The fusion protein obtained will be designated RTS* to distinguish it from the construct obtained with the CSP derived from *P falciparum* strain 7G8.

The sequence of the expression cassette is shown in FIG. 9. It contains the following elements:

A promoter sequence, extending from nucleotide 1 through 1058, derived from the *S. cerevisiae* TDH3 gene.

An open reading frame starting at nucleotide 1059 and extending to nucleotide 2330. This open reading frame is immediately followed by a translational stop codon, TAA (nucleotides 2331 to 2333). The open reading frame encodes the amino acids specifying the hybrid RTS* protein.

A transcription termination sequence contained within the sequence extending from base pair 2334 to 3504, derived from the *S. cerevisiae* ARG3 gene.

This expression cassette encoding this RTS* fusion protein was transformed and integrated into the genome of yeast strain Y1295, using the same approach as described previously for the RTS construct. Transformed clones expressing both the S and RTS* proteins were obtained. One clone was selected expressing the two proteins in a ratio of approximately 4S:1RTS*. The clone was given the laboratory accession number Y1631.

EXAMPLE 6

PRELIMINARY CHARACTERIZATION OF THE STRAIN RIT4383

6.1 Analysis by immunoblotting

Cell free extracts prepared from RIT 4383 were analysed by immunoblot using various antibodies:

a monoclonal antibody directed toward the S protein (Mab HBS1)

a monoclonal antibody directed toward the repeat part of the RTS protein (Mab 167)

a rabbit serum directed toward the repeat-less sequences of the RTS protein (rabbit serum no. 20).

In yeast strain RIT4383, two expressed products were recognized by monoclonal antibody HBS1: a 24 KD protein corresponding to the S protein and a 46 KD RTS hybrid protein. The RTS hybrid protein is also detected by antibodies directed toward repeat and non-repeat epitopes of the CSP. These results indicate clearly that strain RIT4383 simultaneously expresses the two S and RTS antigens at a ratio RTS/S of approximatively 1:4.

6.2 CsCl density gradient centrifugation

The formation of particles in strain RIT4383 was analyzed by CsCl density gradient centrifugation. Crude extract (±15 mg of total protein) was analyzed on a 10 ml 1.5M CsCl gradient (68 hours at 40.000 rpm, +8° C. in a Beckman 50 Ti rotor). Fractions (0.5 ml) were collected and analyzed by a radioimmunoassay specific for HBsAg (AUSRIA), by an RTS specific ELISA and by immunoblot using an anti-HBsAg monoclonal antibody.

Figure 8:
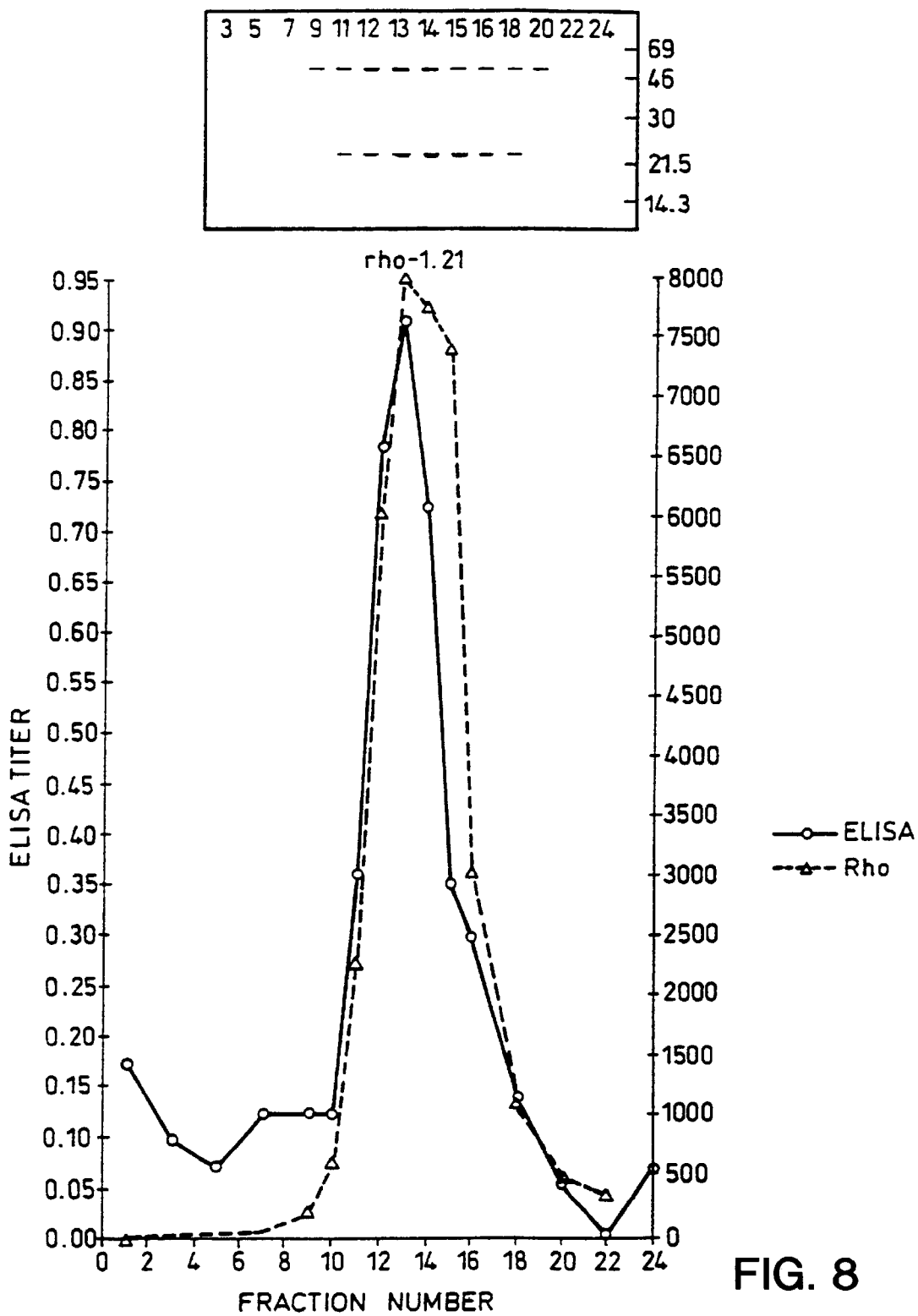
FIG. 8 is a CsCl density analysis of a cell-free extract prepared from strain pRIT4383. Fractions were analyzed by a radioimmunoassay specific for HBsAg (AUSRIA), and by an RTS-specific ELISA. The top panel shows the immunoblot analysis of fractions using an anti-S Mab. The buoyant density (rho) of the peak fraction was calculated from a measure of its refractive index.

As shown in FIG. 8, ELISA, RIA and Western blot peaks appear at the same fraction (no. 13) of the gradient corresponding to a buoyant density of rho=1.21 suggesting that mixed particles, containing both S and RTS monomers, are formed in this strain.

EXAMPLE 7

PREPARATION OF THE SEED LOTS

Production procedure for master seed lot

Strain Y1530 (RIT4383) is first grown for 48 hours at 30° C. in Petri dishes containing 20 ml sterile YNB (Difco) supplemented with dextrose (0.1%) and 1.8% (w/v) agar (Difco). The surface growth is suspended into sterile YNB broth (Difco) supplemented with dextrose (1%) and glycerol (10%). This suspension is distributed under aspectic conditions into 2 ml sterile polypropylene stoppered tubes (1 ml per tube) and stored at −70° C.

Production procedure for working seed lot

One master seed tube is rapidly thawed, and its contents are streaked with a platinum loop on Petri dishes prepared as described above. After incubation at 30° C. for 63 hours, part of the surface growth is transferred to a 2 L conical flask containing 400 ml of sterile YNB broth (Difco) supplemented with dextrose (2%). The culture is incubated at 30° C. for 24 hours before being centrifuged (15 min at 6300×g) under aseptic conditions. The pellet is resuspended into sterile YNB broth (Difco) supplemented with dextrose (1%) and glycerol (10%). This is distributed under aseptic conditions into 2 ml sterile glass stoppered tubes (0.5 ml per tube) and stored at −70° C.

EXAMPLE 8

FERMENTATION

Preparation of the inoculum (a) Growth on solid medium

One vial of the working seed lot is rapidly thawed and spread onto Petri dishes containing sterile YNB broth (Difco) supplemented with dextrose (1%) and 1.8% (w/v) agar (Difco). The Petri dishes are incubated for 48 hours at 30° C.

(b) Growth of inoculum

The surface growth of one Petri dish is suspended in sterile YNB broth (Difco) supplemented with dextrose (2%) and distributed equally into two conical flasks (2 L, 400 ml liquid per flask). The flasks are incubated for 24 hours at 30° C. on a rotary shaker.

Fermentation

The fermentor vessel (20 L total volume) containing 5 L of dieionized water supplemented with $(NH_4)_2SO_4$ (40 g) is sterilized in-situ at 121° C. for 30 minutes using clean, pre-filtered steam at 2 bar g pressure. After cooling to room temperature, the liquid volume in the fermentor is adjusted to 4 L, and 1 L of filter-sterilized HB4 solution is added. The fermentation is begun by adding the inoculum (800 ml) from the two conical flasks.

The fermentation is run using the fed-batch technique whereby the culture is continuously fed with a solution of the following composition.

5 L HB4 solution;

4 L dextrose 80% (sterilized at 121° C.).

The culture density increases by aerobic growth at 30° C. and pH 5 (maintained by addition of $NH_4OH$). Dissolved oxygen is maintained about 50% saturation by adjustment of airflow and agitation speed. The rate of addition of the feed is predetermined to maximize growth rate and minimize formation of by-product ethanol.

The fermentation is stopped after 40–90 hours. At the end of the fermentation, the total culture volume is 10–18 L, and the dry cell weight is between 30 and 100 g/L. The culture is rapidly cooled down to 15–25° C., and the yeast cells are recovered from the broth by centrifugation. The concentrated yeast cells are washed once with phosphate buffer (50 mM) before being re-centifuged and subsequently stored at −70° C. in polyethylene bags.

| HB4 Medium Composition | | |
|---|---|---|
| Component | Quality | |
| $KH_2PO_4$ | 41.00 | g |
| $MgSO_4.7H_2O$ | 23.50 | g |
| $CaCl_2.2H_2O$ | 4.70 | g |
| NaCl | 0.30 | g |
| $FeCl_3.6H_2O$ | 50.00 | mg |
| $H_3BO_3$ | 28.00 | mg |
| $MnSO_4.H_2O$ | 22.40 | mg |
| $ZnSO_4.7H_2O$ | 22.40 | mg |
| $Na_2MoO_4.2H_2O$ | 11.20 | mg |
| KI | 5.60 | mg |
| $CaCl_2.6H_2O$ | 5.10 | mg |
| $CuSO_4.5H_2O$ | 2.24 | mg |
| Biotin | 2.70 | mg |
| Folic acid | 2.70 | mg |
| Inositol | 2.70 | mg |
| Ca Pantothenate | 0.54 | mg |
| Pyridoxin HCl | 0.54 | mg |
| Thiamin.HCl | 0.54 | mg |
| Niacin | 1.20 | mg |
| P-amino benzoic acid | 0.60 | mg |

-continued

| HB4 Medium Composition | | |
|---|---|---|
| Component | Quality | |
| Riboflavin | 0.60 | mg |
| HCl (37° C.) | 5.00 | ml |
| Deionized water (up to) | 1.00 | litre |

EXAMPLE 9

EXTRACTION AND PURIFICATION OF RTS/S

EXTRACTION PROCEDURE 9.1 Preparation of cell suspension

Frozen concentrated yeast cells (at −70° C.) are thawed down to −30° C. overnight and subsequently thawed out to 5–15° C. by placing the polyethylene bags containing the cells in water (10–20° C.). A yeast cell suspension is made with a phosphate buffer solution (pH 8.0) containing the following ingredients: Ethylenediamine tetraacetic acid (EDTA), pMethylsulfonyl Fluoride (PMSF). isopropanol and tween 20.

9.2 Cell disruption

Cells are disrupted in a bead mill containing lead-free glass beads (0.49–0.70 mm diameter). The grinding chamber is cooled by circulation of refrigerating fluid at −20° C., in such a way that the temperature of the homogenate at the outlet of the grinding chamber does not exceed 15° C. The liquid flowrate is 6 L/hour and the agitation speed is 3000 rpm. This process is performed twice. The pH of the resulting homogenate is 6.7 to 7.5.

9.3 Polyethyleneglycol clarification

Polyethyleneglycol 400 (PEG 400) is added to the disrupted cell suspension to give a final concentration of 10% (30 minutes below 10° C., pH 6.1) and a partially-clarified supernatant is recovered by centrifugation (J21B Beckman centrifuge, JA10 rotor at 17,000 g for 1 hour).

9.4 Methanol clarification

Methanol is added at pH 7 to the PEG-clarified antigen to give the proportion of 1 volume of methanol for 5 volumes of PEG-clarified antigen. The clarified antigen is obtained at 17,000 g for 20 minutes by cenrifugation (J21B Beckman centrifuge, JA10 rotor).

9.5 Adsorption/Desorption on colloidal silica

The crude antigen is adsorbed overnight onto 1.5% (w/v) colloidal silica (Aerosil 380, Degussa) at 4° C.

After washing (3 times) the pellet by successive centrifugation and resuspension in NaCl 0.9% (w/v), the antigen is desorbed using a 10 mM pyrophosphate buffer, pH 9.5, containing 1% TWEEN 20.

The desorbing buffer volume corresponds to ⅛ of the methanol clarified antigen solution. The desorbed antigen solution is recovered by ultracentrifugation in a L 8.70 Beckman ultracentrifuge rotor R19 at 50,000 g for 60 minutes.

9.6 Diafiltration

Before the purification steps, the desorbed antigen is washed by ultrafiltration with 5 volumes of urea 6M, NaCl 500 mM, TRIS-HCl 20 mM at pH 8.5 in order to eliminate much of the proteic and lipidic contaminants.

Then the buffer is exchanged in the same system (Ultrasette, FILTRON fitted with polysulfone membranes with a 300 kD nominal cut-off) with 5 volumes of TRIS-HCl 10 mM (ph 8.1).

9.7 Ion exchange chromatography on DEAE-TSK 650 (M)

The clarified solution is applied to an anion-exchange column (DEAE-TSK 650 (M)) equilibrated in a 10 mM TRIS-buffer, pH 8.1. After washing successively with 2 volumes of 10 mM TRIS-HCl buffer pH 8.1 and 3 volumes of 10 mM TRIS-HCl buffer pH 8.1 supplemented with 40 mM NaCl, the antigen is desorbed with less than one volume of 10 mM TRIS-HCl buffer pH 8.1 containing 150 mM NaCl. The antigen-containing fractions are pooled.

9.8 Hydrophobic interaction chromatography on Butyl-TSK 650 (M)

After NaCl addition up to a final concentration of 650 mM NaCl, the antigen solution is loaded on a Butyl-TSK 650 (M) column equilibrated with a 20 mM TRIS-HCl buffer, 600 mM NaCl (pH 8.1). Most of the antigen passes through while most of the impurities bind to the gel.

9.9 Concentration by ultrafiltration

The HIC pool is concentrated by ultrafiltration in an Ultrasette system (FILTRON) fitted with polysulfone membranes with a 300 kDa nominal cut-off.

9.10 Ultracentrifugation in a CsCl gradient

CsCl is added to the Butyl-TSK pool to give a final concenration of 1.5M.

After 65 hours in a 50.2 Ti Beckman rotor at 270,000 g, the antigen-containing fractions are collected.

9.11 Size exclusion chromatography on SEPHACRYL S300 (R Type)

In order to exchange the buffer and to eliminate low molecular weight contaminants, the antigen solution is applied to a SEPHACRYL S300 HR column. The elution buffer is 10 mM phosphate, containing 150 mM NaCl (pH 7.4).

Sterile Filtration

After dilution to between 150 and 400 µg Lowry/ml and pH adjustment to 6.8, the purified antigen is sterilized by filtration through a 0.22 µm sterile filter. The resulting solution contains purified RTS/S particles.

EXAMPLE 10

IMMUNOLOGICAL CHARACTERIZATION OF RTS/S 10.1 Antigenicity

In order to test the antigenicity of the RTS/S particles, a number of ELISAs were performed, combining monoclonal antibodies directed against the different epitopes.

The monoclonal antibodies (MoAbs) used are:

MoAb R10:
  specific for the repeat sequence (NANP) of the CS region.
  IgM isotype.
MoAb RL117:
  specific for the non-repeat sequence of the CSP region.
MoAb RF1:
  specific for the S sequence of the HBsAg.
  IgG1 isotype.

MoAbs R10 and RL117 were prepared in house by fusion of Sp2/OAg 14 myeloma cells with splenocytes of Balb/C mice immunized with partially pure RTS-like particles containing both repeat and non-repeat regions of the CSP sequence.

Three batches of the candidate RTS/S vaccine were analyzed: batches Nos. 24M31, 24M32 and 24M34.

10.2 Reaction with monoclonal antibody R10 (anti-repeat)

The anti-repeat MoAb R10 was used in a "sandwich" ELISA. Samples to be tested were incubated in microtiter plates previously coated with MoAb R10. The same MoAb coupled to peroxidase was then added. After one hour incubation at 37° C. and washing, color was developed by addition of Orthophenylene-diamine-$H_2O_2$. Absorbance was measured at 490 nm and plotted versus the antigen concentration.

Results

The three batches: 24M31, 24M32 and 24M34 reacted positively and consistently with MoAb R10, thus confirming the presence and accessibility of the repeat epitopes on the RTS/S particles. The amount of antigen necessary to reach 50% of maximum binding was 51.2, 38.2 and 60.6 ng for batches 24M31, 24M32 and 24M34 respectively.

10.3 Reaction with monoclonal antibody RL117 (anti-repeatless)

The reactivity of MoAb RL117 with RTS,S particles was analyzed in a "sandwich" ELISA test. MoAb RL117 was coupled to peroxidase and used for the detection of the RTS/S particles, while MoAb R10, specific for the repeat region, was used for the capture of particles Briefly, samples to be tested were incubated in microtiter plates previously coated with MoAb R10. RL117 coupled to peroxidase was then added, and, after one hour incubation at 37° C. and washing, the coloration was developed by addition of Orthophenylene-diamine-$H_2O_2$. Absorbance was measured at 490 nm and plotted versus the antigen concentration.

Results

The three batches: 24M31, 24M32 and 24M34 reacted positively and consistently with MoAbs RL117 and R10, thus confirming the presence and accessibility of repeat and ono-repeat epitopes on the same RTS/S particles. The amount of antigen necessary to reach 50% of maximum binding was 169.2, 117.6 and 181.1 ng for batches 24M31, 24M32 and 24M34 respectively 10.4 Reaction with monoclonal antibody RF1 (anti-S)

The presence of S-epitopes in RTS/S particles was shown by a "sandwich" ELISA test, using MoAb RF1 coupled to peroxidase for detection. The R10 MoAb was used directly onto the microtiter plates in order to capture the RTS,S particles.

In summary, samples to be tested were incubated in microtiter plates previously coated with MoAb R10. MoAb RF1 coupled to peroxidase was then added. After incubation at 37° C. for 1 hour and washing, color development was allowed by addition of Orthophenylene-diamine-$H_2O_2$. Absorbance was measured at 490 nm and plotted versus the antigen concentration.

Results

The three batches: 24M31, 24M32 and 24M34 reacted positively and consistently with MoAbs RF1 and R10, thus confirming the presence and accessibility of the repeat and S epitopes on the same RTS/S particles. The amount of antigen necessary to reach 50% of maximum binding was 52.3, 55.2 and 106.2 ng for batches 24M31, 24M32 and 24M34 respectively.

EXAMPLE 11

IMMUNOGENICITY IN VIVO OF RTS/S PARTICLES 11.1 Immunogenicity studies

Studies on the immunogenicity of (RTS,S) particles were performed in mice and in *Cercopithecus aethiop* monkeys.

In mice, anti-CSP antibodies were analyzed by ELISA test using the R32tet32 antigen for the detection of the anti-repeat antibodies. R32tet32 consists of 32 copies of the NANP (major) repeat fused to a 32 amino acid portion of the tetracyclin resistance gene of plasmid pBR322. The recombinant antigen is produced in *Escherichia coli*. Antibodies (Abs) directed against the non repeated sequence of the CS protein were measured by ELISA test using the RLF antigen. The RLF antigen consists of the complete CS protein flanking region devoid of repeat fused to the first 81 amino acids of the NS1 protein of influenza virus. The RLF antigen is produced in *E. coli*. Mice sera were serially diluted, starting at 1:100, and titers are expressed as the reciprocal of the dilution corresponding to an optical density of 1.0 in the ELISA test (1). Measurements of anti-CSP Abs were performed on individual sera and the geometric mean titer (GMT) was calculated.

In order to analyze the anti-carrier response, anti-HBs antibody titers were also measured (pooled sera only)

In mice experiments, Balb/C mice (H-2d haplotype) usually used for the immunogenicity of HBsAg were also used to evaluate the immunogenicity of RTS,S particles. The intraperitoneal (i.p.) and the subcutaneous (s.c.) routes of immmunization were compared and the effect of the immunostimulant 3-deacylated monophosphoryl lipid A (3D-MPL) on the immune response was also tested The immunogenicity of the (RTS,S) vaccine was also tested in a similar way in *Cercopithecus aethiops* monkeys.

Selected individual or pooled sera were also tested for their capacity to inhibit the in vitro invasion of a human hepatoma cell line (HepG2) by *P. falciparum* sporozoites (ISI assay (2)).

11.2 Immunogenicity in mice

EXPERIMENT 1

Immunogenicity of clinical (RTS,S) batches adsorbed on $Al(OH)_3$

Method

Immunization:

Groups of 10 Balb/C mice were injected twice intraperitoneally at one month interval with 1 µg of each of three (RTS,S) batches previously adsorbed on $Al(OH)_3$ (batches 24M/31, 24M/32 and 24M/34). Control mice were injected with HBsAg (Engerix-B, batch ENG611B4). On days 30 and 45, the mice were bled and the antibody titers were measured on individual sera.

Serological methods:

The anti-R32tet32 and the anti-RLF titers were measured by ELISA using respectively R32tet32 and RLF as coating antigens. The microplates were incubated with the serum sample (12 two-fold serial dilutions starting at 1:100) to be tested. Mouse Abs were reacted with biotinylated anti-mouse Ig followed by streptavidin: biotinylated horseradish peroxidase complex and orthophenylene-diamine/$H_2O_2$. The optical density was measured at 490 nm. The titers were expressed as the reciprocal of the dilution corresponding to an optical density of 1.0 (50% maximal binding). For each group of mice, the geometric mean titer (GMT) was calculated. The anti-HBs antibody titer was calculated according to the Hollinger formula (3) and expressed in mIU/ml.

Results

Anti-CSP response:

Strong anti-R32tet32 and anti-RLF responses were observed for each (RTS,S) batch tested. No significant difference between the batches was noted. A remarkable booster effect was observed after the second dose. Mice immunized with HBsAg ("Engerix-B") were used as negative control in this experiment.

Anti-HBs response:

The (RTS,S) batches induce antibodies directed against the HBsAg carrier protein. The assay was performed on pooled sera only.

EXPERIMENT 2

Effect of the immunostimulant 3D-MPL on the immunogenicity of (RTS,S) particles in Balb/C mice.

We analyzed the effect of the 3D-MPL on the immunogenicity of the (RTS,S) vaccine in mice. Both the intraperitoneal (i.p.) and the subcutaneous (s.c.) routes of immunization were tested.

A. Immunization by the ip route

Method

Immunization:

Groups of 10 Balb/C mice were injected twice intraperitoneally at one month interval with 1 µg of (RTS,S) (batch 24M/34) adsorbed on $Al(OH)_3$ alone or on $Al(OH)_3$+3D-MPL (50 µg/dose). Control mice were injected with NaCl 150 mM. One days 30 and 45, the mice were bled and the antibody titers measured on individual sera.

Serological method:

The serological methods were the same as in the first experiment described above.

Results

Anti-CSP response:

The (RTS,S) vaccine batch induces strong anti-R32tet32 and anti-RLF responses in both formualtions. In all cases, a significant booster effect is observed following the second immunization. Titers obtained with the formulation containing 3D-MPL are in all cases higher than the aluminium alone formulation, and a statistically significant increase was observed in the primary anti-R32tet32 response (p=0.02). A group of mice injected with NaCl 150 mM was used as negative control in this experiment.

Anti-HBs response:

Both formualtions of the (RTS,S) vaccine, injected by the i.p. route, induced a strong anti-HBs response. A significant booster effect was observed following second immunization with either formulation.

B. Immunization by the s.c. route

Method

Immunization:

Groups of 10 Balb/C mice were injected twice subcutaneously at one month interval with 1 µg of (RTS,S), (batch 24M/34) adsorbed on $Al(OH)_3$ alone or on $Al(OH)_3$+3D-MPL (50 µg/dose). Control mice were injected with NaCl 150 mM. One days 30 and 45, the mice were bled and the antibody titers measured on individual sera.

The serological methods were the same as in the first experiment described above.

Results

Anti-CSP response:

The (RTS,S) vaccine batch induced positive response against R32tet32 and RLF in both formulations. In all cases, a significant booster effect was observed following the second immunization. Statistically significant higher titers were observed with the 3D-MPL formulation on day 45, both for the anti-R32tet32 and anti-RLF responses (p=0.18 and p=2.9 respectively). In general, however, titers were lower than those obtained with the i.p. route. A group of mice injected with NaCl 150 mM was used as negative control in this experiment.

Anti-HBs response:

Both formulations of the (RTS,S) vaccine, injected by the s.c. route induced a good anti-HBs response. A significant booster effect was observed following second immunization with either formulation. As observed for the anti-CSP responses, the anti-HBs response was lower by this route of immunization as compared to the i.p. route.

11.3 Immunogenicity in *Cercopithecus aethiops*

The immunogenicity was evaluated in *Cercopithecus aethiops* monkeys with clinical batch 24M/32 adsorbed on $Al(OH)_3$.

Methods

Immunization:

Five monkeys were injected intramuscularly on days 0, 28 and 84 with 20 µg of (RTS,S) particles adsorbed on $Al(OH)_3$ (0.5 mg Al+++). The animals were bled on days 0, 14, 28, 42, 56, 66 and 98. Antibodies directed against R32tet32, RLF and HBs antigens were measured.

Serological methods:

Anti-R32tet32 and the anti-RLF antibody titers were measured by ELISA using respectively the R32tet32 and the RLF antigens coated on microplates. The plates were then incubated with the serum sample to be tested (12 two-fold serial dilutions starting at 1:10). Monkey antibodies were detected by biotinylated anti-human Ig followed by streptavidin biotinylated horseradish peroxidase complex and orthophenylenediamine/$H_2O_2$. The optical density was measured at 490 nm. The titers were expressed as the reciprocal of the dilution corresponding to an optical density of 1.0 (50% maximal binding). For each group, the geometric mean titer (GMT) was calculated. The anti-HBs antibody titers were calculated according to the Hollinger formula (Hollinger et al., 1982) and expressed in mIU/ml.

Results

Anti-CSP response:

The (RTS,S) vaccine induced a positive response against both R32tet32 and RLF antigens in all 5 monkeys. A significant booster effect was observed 14 days following second immunization (day 42). A slow decrease of antibody titers was then observed up to the third immunization. The titers again increase 14 days following the third immunization (day 98), expect in the case of the anti-RLF response of monkey Jo 352.

The anti-R32tet32 titers reached after the third immunization (day 98) are not however higher than those observed after the second immunization (day 42).

In the case of the anti-RLF response (with the exception of monkey JO 353), an increase of titers is observed following the third immunization (day 98) relative to post second immunization levels (day 42).

Anti-HBs response:

All monkeys raised an anti-HBs response with significant booster effects following second (day 42) as well as third (day 98) immunization.

Biological activity of antibodies raised against the (RTS,S) particle

As a measure of the biological function of the antibodies induced by the (RTS,S) vaccine, pooled mice and individual monkeys sera were tested by the Inhibition of Sporozoite Invasion (ISI) assay Hollingdale et al., 1984). This assay measured the capacity of the anti-CSP antibodies to inhibit the in vitro invasion of a human hepatoma cell line (HepG2) by P. falciparum sporozoites.

Results

The results of this experiment are presented in Tables 1 and 2. The ISI data are expressed as % inhibition relative to the activity of a pre-immune control serum taken as 0% inhibition. For reference, the anti-R32tet32 and RLF antibody titers of the tested sera are included. Table 1 shows that all mice sera tested have very high ISI activity. Table 2 shows that all 5 monkeys have also a very ISI activity on day 98 compared with the corresponding immune serum.

Conclusion

The (RTS,S) particles induced, both in mice and monkeys, a high antibody response directed against the repeat and non-repeat epitopes of the CSP and against the S protein of the HBsAg carrier.

The primary antibody response in mice was enhanced by the presence of 3D-MPL.

Antibody titers obtained after intraperitoneal injection were higher than those obtained after immunization by the subcutaneous route.

The antibodies elicited in the two animal species effectively prevented invasion of cultured human hepatoma cells by P. falciparum sporozoites.

DEPOSIT

Yeast strain RIX 4397 (Laboratory Accession number Y1631) has been deposited with the Belgian Coordinated Collections of Microorganism (BCCM), Scientific Institute of Public Health—Louis Pasteur—Mycology, J. Wytsmanstraat 14 Rue J. Wystsman, B-1050 Brussells, Belgium under the terms of the Budapest Treaty on Sep. 23, 1998 under Accession Number IHEM 14798. Yeast strain RIX 4383 (Laboratory Accession number Y1530) has been deposited with BCCM under the terms of the Budapest Treaty on Sep. 23, 1998 under Accession number IHEM 14799.

TABLE 1

ISI activity of sera from Balb/C mice immunized with TS.S

| Pool of Mice sera | A-R32tet32 Titer | A-RLF Titer | ISI (%) |
|---|---|---|---|
| Pool i.p A1 + 3D-MPL Day 45 | 606544 | 242408 | 100% |
| Pool i.p Alum only Day 45 | 87005 | 160284 | 98% |
| Pool i.p A1 + 3D-MPL Day 45 | 15333 | 99002 | 94% |
| Pool s.c A1 + 3D-MPL Day 45 | 5102 | 20453 | 86% |
| Pool of Negative Controls | 205 | 205 | 0% |

TABLE 2

ISI activity of individual monkey sera immunized with RTS.S

| Monkey # | Serum | A-R32tet32 titer | A-RLF titer | ISI (%) |
|---|---|---|---|---|
| J0 352 | DAY 0 | <50 | <50 | 0% |
|  | DAY 98 | 1762 | 1250 | 98% |
| J0 353 | DAY 0 | <50 | <50 | 0% |
|  | DAY 98 | 1574 | 32218 | 90% |
| J0 354 | DAY 0 | <50 | <50 | 0% |
|  | DAY 98 | 3751 | 31034 | 98% |
| J0 356 | DAY 0 | <50 | <50 | 0% |
|  | DAY 98 | 1495 | 18544 | 95% |
| J0 357 | DAY 0 | <50 | <50 | 0% |
|  | DAY 98 | 1420 | 30727 | 98% |

REFERENCE (1) Harford N., Cabezon T., Colau B., et al., "Construction and Characterization of a Saccharomyces cerevisiae Strain (RIT4376) Expressing Hepatitis B Surface Antigen", Postgrad Med J 63, Supp. 2: 65–70, 1987.
(2) Jacobs E., Rutgers T., Voet P., et al., "Simultaneous Synthesis and Assembly of Various Hepatitis B Surface Proteins in Saccharomyces cerevisiae", Gene 80: 279–291, 1989.
(3) Vieira J. and Messing J., "The pUC plasmids, an M13mp7-Derived System for Insertion Mutagenesis and Sequencing with Synthetic Universal Primers", *Gene 19: 259–268, 1982.

(4) Juniaux *Embo J* 1: 1125–1131, 1982.
(5) Hinnen A., Hicks J. B., and Fink G. R., "Transformation of Yeast", *Proc Natl Acad Sci USA* 75: 1929–1933, 1980.
(6) Broach J. R., Strathern J. N., and Hicks J. B., "Transformation in Yeast Development of a Hybrid Cloning Vector and Isolation of the CAN 1 Gene", *Gene* 8: 121–133, 1979.
(7) Zhang H., et. al., "Double Stranded SDNA Sequencing as a Choice for DNA Sequencing", *Nucleic Acids Research* 16: 1220, 1988.
(8) Dame J. B., Williams J. L. Mc Cutchan T. F., et al., "Structure of the Gene Encoding the Immunodominant Surface Antigen on the Sporozoites of the Human Malaria Parasite *Plasmodium falciparum*", *Science* 225: 593–599, 1984.
(9) Valenzuela P., Gray P., Quiroga M., et al., "Nucleotide Sequences of the Gene Coding for the Major Protein of Hepatitis B Virus Surface Antigen", *Nature* 280: 815–819, 1979.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 423 amino acids
        (B) TYPE: amino acid
        (C) STRANDEDNESS: single
        (D) TOPOLOGY: linear (xi) SEQUENCE DESCRIPTION: SEQ ID NO:1:

```
Met Met Ala Pro Asp Pro Asn Ala Asn Pro Asn Ala Asn Pro Asn Ala
 1               5                  10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
            35                  40                  45

Asn Pro Asn Ala Asn Pro Asn Ala Asn Pro Asn Ala Asn Pro Asn Ala
50                  55                  60

Asn Pro Asn Ala Asn Pro Asn Ala Asn Pro Asn Ala Asn Pro Asn Ala
65                  70                  75                  80

Asn Pro Asn Lys Asn Asn Gln Gly Asn Gly Gln Gly His Asn Met Pro
                85                  90                  95

Asn Asp Pro Asn Arg Asn Val Asp Glu Asn Asn Ala Asn Asn Ala Val
            100                 105                 110

Lys Asn Asn Asn Glu Glu Pro Ser Asp Lys His Ile Glu Gln Tyr
            115                 120                 125

Leu Lys Lys Ile Lys Asn Ser Ile Ser Thr Glu Trp Ser Pro Cys Ser
            130                 135                 140

Val Thr Cys Gly Asn Gly Ile Gln Val Arg Ile Lys Pro Gly Ser Ala
145                 150                 155                 160

Asn Lys Pro Lys Asp Glu Leu Asp Tyr Glu Asn Asp Ile Glu Lys Lys
                165                 170                 175

Ile Cys Lys Met Glu Lys Cys Ser Ser Val Phe Asn Val Val Asn Ser
            180                 185                 190

Arg Pro Val Thr Asn Met Glu Asn Ile Thr Ser Gly Phe Leu Gly Pro
            195                 200                 205

Leu Leu Val Leu Gln Ala Gly Phe Phe Leu Leu Thr Arg Ile Leu Thr
    210                 215                 220

Ile Pro Gln Ser Leu Asp Ser Trp Trp Thr Ser Leu Asn Phe Leu Gly
225                 230                 235                 240

Gly Ser Pro Val Cys Leu Gly Gln Asn Ser Gln Ser Pro Thr Ser Asn
            245                 250                 255

His Ser Pro Thr Ser Cys Pro Pro Ile Cys Pro Gly Tyr Arg Trp Met
```

```
                260                 265                 270
    Cys Leu Arg Arg Phe Ile Ile Phe Leu Phe Ile Leu Leu Cys Leu
                275                 280                 285
    Ile Phe Leu Leu Val Leu Leu Asp Tyr Gln Gly Met Leu Pro Val Cys
    290                 295                 300
    Pro Leu Ile Pro Gly Ser Thr Thr Thr Asn Thr Gly Pro Cys Lys Thr
    305                 310                 315                 320
    Cys Thr Thr Pro Ala Gln Gly Asn Ser Met Phe Pro Ser Cys Cys Cys
                    325                 330                 335
    Thr Lys Pro Thr Asp Gly Asn Cys Thr Cys Ile Pro Ile Pro Ser Ser
                    340                 345                 350
    Trp Ala Phe Ala Lys Tyr Leu Trp Glu Trp Ala Ser Val Arg Phe Ser
                    355                 360                 365
    Trp Leu Ser Leu Leu Val Pro Phe Val Gln Trp Phe Val Gly Leu Ser
    370                 375                 380
    Pro Thr Val Trp Leu Ser Ala Ile Trp Met Met Trp Tyr Trp Gly Pro
    385                 390                 395                 400
    Ser Leu Tyr Ser Ile Val Ser Pro Phe Ile Pro Leu Leu Pro Ile Phe
                    405                 410                 415
    Phe Cys Leu Trp Val Tyr Ile
                    420
```

(2) INFORMATION FOR SEQ ID NO:2:

(i) SEQUENCE CHARACTERISTICS:
        (A) LENGTH: 3504 base pairs
        (B) TYPE: nucleic acid
        (C) STRANDEDNESS: single
        (D) TOPOLOGY: linear (xi) SEQUENCE DESCRIPTION: SEQ ID NO:2:

```
AAGCTTACCA GTTCTCACAC GGAACACCAC TAATGGACAC AAATTCGAAA TACTTTGACC    60

CTATTTTCGA GGACCTTGTC ACCTTGAGCC CAAGAGAGCC AAGATTTAAA TTTTCCTATG   120

ACTTGATGCA AATTCCCAAA GCTAATAACA TGCAAGACAC GTACGGTCAA GAAGACATAT   180

TTGACCTCTT AACTGGTTCA GACGCGACTG CCTCATCAGT AAGACCCGTT GAAAAGAACT   240

TACCTGAAAA AAACGAATAT ATACTAGCGT TGAATGTTAG CGTCAACAAC AAGAAGTTTA   300

ATGACGCGGA GGCCAAGGCA AAAAGATTCC TTGATTACGT AAGGGAGTTA GAATCATTTT   360

GAATAAAAAA CACGCTTTTT CAGTTCGAGT TTATCATTAT CAATACTGCC ATTTCAAAGA   420

ATACGTAAAT AATTAATAGT AGTGATTTTC CTAACTTTAT TTAGTCAAAA ATTAGCCTTT   480

TAATTCTGCT GTAACCCGTA CATGCCCAAA ATAGGGGGCG GGTTACACAG AATATATAAC   540

ATCGTAGGTG TCTGGGTGAA CAGTTTATCC CTGGCATCCA CTAAATATAA TGGAGCTCGC   600

TTTTAAGCTG GCATCCAGAA AAAAAAGAA TCCCAGCACC AAAATATTGT TTTCTTCACC    660

AACCATCAGT TCATAGGTCC ATTCTCTTAG CGCAACTACA GAGAACAGGG GCACAAACAG   720

GCAAAAAACG GCACAACCT CAATGGAGTG ATGCAACCTG CCTGGAGTAA ATGATGACAC    780

AAGGCAATTG ACCCACGCAT GTATCTATCT CATTTTCTTA CACCTTCTAT TACCTTCTGC   840

TCTCTCTGAT TTGGAAAAAG CTGAAAAAAA AGGTTGAAAC CAGTTCCCTG AAATTATTCC   900

CCTACTTGAC TAATAAGTAT ATAAAGACGG TAGGTATTGA TTGTAATTCT GTAAATCTAT   960

TTCTTAAACT TCTTAAATTC TACTTTTATA GTTAGTCTTT TTTTTAGTTT TAAAACACCA  1020

AGAACTTAGT TTCGAATAAA CACACATAAA CAAACAAAAT GATGGCTCCC GATCCTAATG  1080

CAAATCCAAA TGCAAACCCA AATGCAAACC CAAACGCAAA CCCCAATGCA AATCCTAATG  1140
```

```
CAAACCCCAA TGCAAATCCT AATGCAAATC CTAATGCCAA TCCAAATGCA AATCCAAATG    1200

CAAACCCAAA CGCAAACCCC AATGCAAATC CTAATGCCAA TCCAAATGCA AATCCAAATG    1260

CAAACCCAAA TGCAAACCCA AATGCAAACC CCAATGCAAA TCCTAATAAA AACAATCAAG    1320

GTAATGGACA AGGTCACAAT ATGCCAAATG ACCCAAACCG AAATGTAGAT GAAAATGCTA    1380

ATGCCAACAA TGCTGTAAAA AATAATAATA ACGAAGAACC AAGTGATAAG CACATAGAAC    1440

AATATTTAAA GAAAATAAAA AATTCTATTT CAACTGAATG GTCCCCATGT AGTGTAACTT    1500

GTGGAAATGG TATTCAAGTT AGAATAAAGC CTGGCTCTGC TAATAAACCT AAAGACGAAT    1560

TAGATTATGA AAATGATATT GAAAAAAAAA TTTGTAAAAT GGAAAAGTGC TCGAGTGTGT    1620

TTAATGTCGT AAATAGTCGA CCTGTGACGA ACATGGAGAA CATCACATCA GGATTCCTAG    1680

GACCCCTGCT CGTGTTACAG GCGGGGTTTT TCTTGTTGAC AAGAATCCTC ACAATACCGC    1740

AGAGTCTAGA CTCGTGGTGG ACTTCTCTCA ATTTTCTAGG GGGATCACCC GTGTGTCTTG    1800

GCCAAAATTC GCAGTCCCCA ACCTCCAATC ACTCACCAAC CTCCTGTCCT CCAATTTGTC    1860

CTGGTTATCG CTGGATGTGT CTGCGGCGTT TTATCATATT CCTCTTCATC CTGCTGCTAT    1920

GCCTCATCTT CTTATTGGTT CTTCTGGATT ATCAAGGTAT GTTGCCCGTT TGTCCTCTAA    1980

TTCCAGGATC AACAACAACC AATACGGGAC CATGCAAAAC CTGCACGACT CCTGCTCAAG    2040

GCAACTCTAT GTTTCCCTCA TGTTGCTGTA CAAAACCTAC GGATGGAAAT TGCACCTGTA    2100

TTCCCATCCC ATCGTCCTGG GCTTTCGCAA ATACCTATG GGAGTGGGCC TCAGTCCGTT     2160

TCTCTTGGCT CAGTTTACTA GTGCCATTTG TTCAGTGGTT CGTAGGGCTT TCCCCCACTG    2220

TTTGGCTTTC AGCTATATGG ATGATGTGGT ATTGGGGGCC AAGTCTGTAC AGCATCGTGA    2280

GTCCCTTTAT ACCGCTGTTA CCAATTTTCT TTTGTCTCTG GGTATACATT TAACGAATTC    2340

CAAGCTGAAA CAATTCAAAG GTTTTCAAAT CAATCAAGAA CTTGTCTCTG TGGCTGATCC    2400

AAACTACAAA TTTATGCATT GTCTGCCAAG ACATCAAGAA GAAGTTAGTG ATGATGTCTT    2460

TTATGGAGAG CATTCCATAG TCTTTGAAGA AGCAGAAAAC AGATTATATG CAGCTATGTC    2520

TGCCATTGAT ATCTTTGTTA ATAATAAAGG TAATTTCAAG GACTTGAAAT AATCCTTCTT    2580

TCGTGTTCTT AATAACTAAT ATATAAATAC AGATATAGAT GCATGAATAA TGATATACAT    2640

TGATTATTTT GCAATGTCAA TTAAAAAAAA AAAATGTTAG TAAAACTATG TTACATTCCA    2700

AGCAAATAAA GCACTTGGTT AAACGAAATT AACGTTTTTA AGACAGCCAG ACCGCGGTCT    2760

AAAAATTTAA ATATACACTG CCAACAAATT CCTTCGAGTT GTCCAATTTC ACCACTTTTA    2820

TATTTTCATC AACTTCAGCA GATTCAACCT TCTCACATAG AACATTGGAA TAAACAGCCT    2880

TAACACCACT TTCAAGTTTG CACAGCGTAA TATGAGGAAT TTTGTTTTGA CAACACAACC    2940

CTTTAATTTT CTCATTGTTT TCATCAATTA TGCATCCATC TTTATCTTTA GACAGTTCCA    3000

CTACAATAGC AATAGTTTTT TCATCCCAAC ATAGTTTTTC GAGCCTAAAA TTCAGTTTGT    3060

CGGTCGTTTT TACCTGCGTA TTTTGGTTAT TACCAGAGCC TTGTGCATTT TCTATGCGGT    3120

TGTTATTGTA CTCCGTTATC TGGTCAGTGT ATCTGTTACA ATATGATTCC ACAACTTTTT    3180

TGCCTCTTTT TCACGGGACG ACATGACATG ACCTAATGTT ATATGAAGTT CCTTCTGAAC    3240

TTTTCCACTA GCTAGTAAAT GCTTGAATTT CTCAGTCAGC TCTGCATCGC TAGCAATACA    3300

CCTCTTGACC AATTCAATAA TTTCATCGTA GTTTTCTATT TAGCTGAGAT ATATGTAGGT    3360

TTAATTAACT TAGCGTTTTT TGTTGATTAT TGTTGCCTTT ACCAACTATT TTTCTCACAG    3420

TAGGTTTGTA ATCTAAGCTC CTTCTGAACG CTGTCTCAAT TTCATCATCT TTCGGGATCT    3480

CTGGTACCAA AATTGGATAA GCTT                                          3504
```

(2) INFORMATION FOR SEQ ID NO:3:

(i) SEQUENCE CHARACTERISTICS:
        (A) LENGTH: 424 amino acids
        (B) TYPE: amino acid
        (C) STRANDEDNESS: single
        (D) TOPOLOGY: linear (xi) SEQUENCE DESCRIPTION: SEQ ID NO:3:

```
Met Met Ala Pro Asp Pro Asn Ala Asn Pro Asn Ala Asn Pro Asn Ala
 1               5                  10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Lys
65                  70                  75                  80

Asn Asn Gln Gly Asn Gly Gln Gly His Asn Met Pro Asn Asp Pro Asn
                85                  90                  95

Arg Asn Val Asp Glu Asn Ala Asn Ala Asn Ser Ala Val Lys Asn Asn
                100                 105                 110

Asn Asn Glu Glu Pro Ser Asp Lys His Ile Lys Glu Tyr Leu Asn Lys
            115                 120                 125

Ile Gln Asn Ser Leu Ser Thr Glu Trp Ser Pro Cys Ser Val Thr Cys
        130                 135                 140

Gly Asn Gly Ile Gln Val Arg Ile Lys Pro Gly Ser Ala Asn Lys Pro
145                 150                 155                 160

Lys Asp Glu Leu Asp Tyr Ala Asn Asp Ile Glu Lys Lys Ile Cys Lys
                165                 170                 175

Met Glu Lys Cys Ser Ser Val Phe Asn Val Val Asn Ser Ser Ile Gly
                180                 185                 190

Leu Gly Pro Val Thr Asn Met Glu Asn Ile Thr Ser Gly Phe Leu Gly
            195                 200                 205

Pro Leu Leu Val Leu Gln Ala Gly Phe Phe Leu Leu Thr Arg Ile Leu
        210                 215                 220

Thr Ile Pro Gln Ser Leu Asp Ser Trp Trp Thr Ser Leu Asn Phe Leu
225                 230                 235                 240

Gly Gly Ser Pro Val Cys Leu Gly Gln Asn Ser Gln Ser Pro Thr Ser
                245                 250                 255

Asn His Ser Pro Thr Ser Cys Pro Pro Ile Cys Pro Gly Tyr Arg Trp
                260                 265                 270

Met Cys Leu Arg Arg Phe Ile Ile Phe Leu Phe Ile Leu Leu Leu Cys
            275                 280                 285

Leu Ile Phe Leu Leu Val Leu Leu Asp Tyr Gln Gly Met Leu Pro Val
        290                 295                 300

Cys Pro Leu Ile Pro Gly Ser Thr Thr Thr Asn Thr Gly Pro Cys Lys
305                 310                 315                 320

Thr Cys Thr Thr Pro Ala Gln Gly Asn Ser Met Phe Pro Ser Cys Cys
                325                 330                 335

Cys Thr Lys Pro Thr Asp Gly Asn Cys Thr Cys Ile Pro Ile Pro Ser
                340                 345                 350

Ser Trp Ala Phe Ala Lys Tyr Leu Trp Glu Trp Ala Ser Val Arg Phe
            355                 360                 365
```

Ser Trp Leu Ser Leu Leu Val Pro Phe Val Gln Trp Phe Val Gly Leu
    370                 375                 380

Ser Pro Thr Val Trp Leu Ser Ala Ile Trp Met Met Trp Tyr Trp Gly
385                 390                 395                 400

Pro Ser Leu Tyr Ser Ile Val Ser Pro Phe Ile Pro Leu Leu Pro Ile
                405                 410                 415

Phe Phe Cys Leu Trp Val Tyr Ile
            420

(2) INFORMATION FOR SEQ ID NO:4:

(i) SEQUENCE CHARACTERISTICS:
        (A) LENGTH: 3504 base pairs
        (B) TYPE: nucleic acid
        (C) STRANDEDNESS: single
        (D) TOPOLOGY: linear (xi) SEQUENCE DESCRIPTION: SEQ ID NO:4:

```
AAGCTTACCA GTTCTCACAC GGAACACCAC TAATGGACAC AAATTCGAAA TACTTTGACC    60

CTATTTTCGA GGACCTTGTC ACCTTGAGCC AAGAGAGCC AAGATTTAAA TTTTCCTATG    120

ACTTGATGCA AATTCCCAAA GCTAATAACA TGCAAGACAC GTACGGTCAA GAAGACATAT   180

TTGACCTCTT AACTGGTTCA GACGCGACTG CCTCATCAGT AAGACCCGTT GAAAAGAACT   240

TACCTGAAAA AAACGAATAT ATACTAGCGT TGAATGTTAG CGTCAACAAC AAGAAGTTTA   300

ATGACGCGGA GGCCAAGGCA AAAGATTCC TTGATTACGT AAGGGAGTTA GAATCATTTT    360

GAATAAAAAA CACGCTTTTT CAGTTCGAGT TTATCATTAT CAATACTGCC ATTTCAAAGA   420

ATACGTAAAT AATTAATAGT AGTGATTTTC CTAACTTTAT TTAGTCAAAA ATTAGCCTTT   480

TAATTCTGCT GTAACCCGTA CATGCCCAAA ATAGGGGCG GGTTACACAG AATATATAAC    540

ATCGTAGGTG TCTGGGTGAA CAGTTTATCC CTGGCATCCA CTAAATATAA TGGAGCTCGC   600

TTTTAAGCTG GCATCCAGAA AAAAAAGAA TCCCAGCACC AAAATATTGT TTTCTTCACC    660

AACCATCAGT TCATAGGTCC ATTCTCTTAG CGCAACTACA GAGAACAGGG GCACAAACAG   720

GCAAAAAACG GCACAACCT CAATGGAGTG ATGCAACCTG CCTGGAGTAA ATGATGACAC    780

AAGGCAATTG ACCCACGCAT GTATCTATCT CATTTTCTTA CACCTTCTAT TACCTTCTGC   840

TCTCTCTGAT TTGGAAAAAG CTGAAAAAAA AGGTTGAAAC CAGTTCCCTG AAATTATTCC   900

CCTACTTGAC TAATAAGTAT ATAAAGACGG TAGGTATTGA TTGTAATTCT GTAAATCTAT   960

TTCTTAAACT TCTTAAATTC TACTTTTATA GTTAGTCTTT TTTTTAGTTT TAAAACACCA   1020

AGAACTTAGT TTCGAATAAA CACACATAAA CAAACAAAAT GATGGCTCCC GATCCTAATG   1080

CAAATCCAAA TGCAAACCCA AACGCAAACC CCAATGCAAA TCCTAATGCA AACCCCAATG   1140

CAAATCCTAA TGCAAATCCT AATGCCAATC CAAATGCAAA TCCAAATGCA AACCCAAACG   1200

CAAACCCCAA TGCAAATCCT AATGCCAATC CAAATGCAAA TCCAAATGCA AACCCAAATG   1260

CAAACCCAAA TGCAAACCCC AATGCAAATC CTAATAAAAA CAATCAAGGT AATGGACAAG   1320

GTCACAATAT GCCAAATGAC CCAAACCGAA ATGTAGATGA AAATGCTAAT GCCAACAGTG   1380

CTGTAAAAAA TAATAATAAC GAAGAACCAA GTGATAAGCA CATAAAAGAA TATTTAAACA   1440

AAATACAAAA TTCTCTTTCA ACTGAATGGT CCCCATGTAG TGTAACTTGT GGAAATGGTA   1500

TTCAAGTTAG AATAAAGCCT GGCTCTGCTA ATAAACCTAA AGACGAATTA GATTATGCAA   1560

ATGATATTGA AAAAAAAATT TGTAAATGG AAAAATGTTC CAGTGTGTTT AATGTCGTAA    1620

ATAGTTCAAT AGGATTAGGG CCTGTGACGA ACATGGAGAA CATCACATCA GGATTCCTAG   1680
```

-continued

```
GACCCCTGCT CGTGTTACAG GCGGGGTTTT TCTTGTTGAC AAGAATCCTC ACAATACCGC    1740
AGAGTCTAGA CTCGTGGTGG ACTTCTCTCA ATTTTCTAGG GGGATCACCC GTGTGTCTTG    1800
GCCAAAATTC GCAGTCCCCA ACCTCCAATC ACTCACCAAC CTCCTGTCCT CCAATTTGTC    1860
CTGGTTATCG CTGGATGTGT CTGCGGCGTT TTATCATATT CCTCTTCATC CTGCTGCTAT    1920
GCCTCATCTT CTTATTGGTT CTTCTGGATT ATCAAGGTAT GTTGCCCGTT TGTCCTCTAA    1980
TTCCAGGATC AACAACAACC AATACGGGAC CATGCAAAAC CTGCACGACT CCTGCTCAAG    2040
GCAACTCTAT GTTTCCCTCA TGTTGCTGTA CAAAACCTAC GGATGGAAAT TGCACCTGTA    2100
TTCCCATCCC ATCGTCCTGG GCTTTCGCAA AATACCTATG GGAGTGGGCC TCAGTCCGTT    2160
TCTCTTGGCT CAGTTTACTA GTGCCATTTG TTCAGTGGTT CGTAGGGCTT TCCCCCACTG    2220
TTTGGCTTTC AGCTATATGG ATGATGTGGT ATTGGGGGCC AAGTCTGTAC AGCATCGTGA    2280
GTCCCTTTAT ACCGCTGTTA CCAATTTTCT TTTGTCTCTG GGTATACATT TAACGAATTC    2340
CAAGCTGAAA CAATTCAAAG GTTTTCAAAT CAATCAAGAA CTTGTCTCTG TGGCTGATCC    2400
AAACTACAAA TTTATGCATT GTCTGCCAAG ACATCAAGAA GAAGTTAGTG ATGATGTCTT    2460
TTATGGAGAG CATTCCATAG TCTTTGAAGA AGCAGAAAAC AGATTATATG CAGCTATGTC    2520
TGCCATTGAT ATCTTTGTTA ATAATAAAGG TAATTTCAAG GACTTGAAAT AATCCTTCTT    2580
TCGTGTTCTT AATAACTAAT ATATAAATAC AGATATAGAT GCATGAATAA TGATATACAT    2640
TGATTATTTT GCAATGTCAA TTAAAAAAAA AAAATGTTAG TAAAACTATG TTACATTCCA    2700
AGCAAATAAA GCACTTGGTT AAACGAAATT AACGTTTTTA AGACAGCCAG ACCGCGGTCT    2760
AAAAATTTAA ATATACACTG CCAACAAATT CCTTCGAGTT GTCCAATTTC ACCACTTTTA    2820
TATTTTCATC AACTTCAGCA GATTCAACCT TCTCACATAG AACATTGGAA TAAACAGCCT    2880
TAACACCACT TTCAAGTTTG CACAGCGTAA TATGAGGAAT TTTGTTTTGA CAACACAACC    2940
CTTTAATTTT CTCATTGTTT TCATCAATTA TGCATCCATC TTTATCTTTA GACAGTTCCA    3000
CTACAATAGC AATAGTTTTT TCATCCCAAC ATAGTTTTTC GAGCCTAAAA TTCAGTTTGT    3060
CGGTCGTTTT TACCTGCGTA TTTTGGTTAT TACCAGAGCC TTGTGCATTT TCTATGCGGT    3120
TGTTATTGTA CTCCGTTATC TGGTCAGTGT ATCTGTTACA ATATGATTCC ACAACTTTTT    3180
TGCCTCTTTT TCACGGGACG ACATGACATG ACCTAATGTT ATATGAAGTT CCTTCTGAAC    3240
TTTTCCACTA GCTAGTAAAT GCTTGAATTT CTCAGTCAGC TCTGCATCGC TAGCAATACA    3300
CCTCTTGACC AATTCAATAA TTTCATCGTA GTTTTCTATT TAGCTGAGAT ATATGTAGGT    3360
TTAATTAACT TAGCGTTTTT TGTTGATTAT TGTTGCCTTT ACCAACTATT TTTCTCACAG    3420
T

7. A multimeric lipoprotein particle comprising the hybrid protein of claim 1 and HBsAg.

8. A multimeric lipoprotein particle comprising the hybrid protein of claim 2 and HBsAg.

9. A multimeric lipoprotein particle comprising the hybrid protein of claim 3 and HBsAg.

10. A multimeric lipoprotein particle comprising the hybrid protein of claim 4 and HBsAg.

11. A multimeric lipoprotein particle comprising the hybrid protein of claim 5 and HBsAg.

12. A multimeric lipoprotein particle comprising the hybrid protein of claim 6 and HBsAg.

13. The particle according to claim 7 wherein the ratio of hybrid protein to S protein is 1:4.

14. The particle according to claim 8 wherein the ratio of hybrid protein to S protein is 1:4.

15. The particle according to claim 9 wherein the ratio of hybrid protein to S protein is 1:4.

16. The particle according to claim 10 wherein the ratio of hybrid protein to S protein is 1:4.

17. The particle according to claim 11 wherein the ratio of hybrid protein to S protein is 1:4.

18. The particle according to claim 12 wherein the ratio of hybrid protein to S protein is 1:4.

19. A vaccine comprising an immunoprotective amount of a protein according to claim 1 in admixture with a suitable diluent.

20. A vaccine comprising an immunoprotective amount of a protein according to claim 5 in admixture with a suitable diluent.

21. A vaccine comprising an immunoprotective amount of a protein according to claim 6 in admixture with a suitable diluent.

22. A vaccine comprising an immunoprotective amount of a particle according to claim 7 in admixture with a suitable diluent.

23. A vaccine comprising an immunoprotective amount of a particle according to claim 11 in admixture with a suitable diluent.

24. A vaccine comprising an immunoprotective amount of a particle according to claim 12 in admixture with a suitable diluent.

25. The vaccine according to claim 19 additionally comprising one or more of the group consisting of 3-deacylated monophosphoryl lipid A, alum, saponins and an oil and water emulsion.

26. The vaccine according to claim 20 additionally comprising one or more of the group consisting of 3-deacylated monophosphoryl lipid A, alum, saponins and an oil and water emulsion.

27. The vaccine according to claim 21 additionally comprising one or more of the group consisting of 3-deacylated monophosphoryl lipid A, alum, saponins and an oil and water emulsion.

28. The vaccine according to claim 22 additionally comprising one or more of the group consisting of 3-deacylated monophosphoryl lipid A, alum, saponins and an oil and water emulsion.

29. The vaccine according to claim 23 additionally comprising one or more of the group consisting of 3-deacylated monophosphoryl lipid A, alum, saponins and an oil and water emulsion.

30. The vaccine according to claim 24 additionally comprising one or more of the group consisting of 3-deacylated monophosphoryl lipid A, alum, saponins and an oil and water emulsion.

31. A method of vaccinating a patient susceptible to Plasmodium infections comprising administering an effective amount of the vaccine according to claim 19.

32. A method of vaccinating a patient susceptible to Plasmodium infections comprising administering an effective amount of the vaccine according to claim 20.

33. A method of vaccinating a patient susceptible to Plasmodium infections comprising administering an effective amount of the vaccine according to claim 21.

34. A method of vaccinating a patient susceptible to Plasmodium infections comprising administering an effective amount of the vaccine according to claim 22.

35. A method of vaccinating a patient susceptible to Plasmodium infections comprising administering an effective amount of the vaccine according to claim 23.

36. A method of vaccinating a patient susceptible to Plasmodium infections comprising administering an effective amount of the vaccine according to claim 24.

37. The hybrid protein of claim 2 wherein the CS protein is fused in frame to the N-terminal of HBsAg via a linear linker.

38. A hybrid protein comprising the following amino acid residues:

a) an N-terminal methionine residue;

b) Met-Ala-Pro;

c) a stretch of 189 amino acids corresponding to amino acids 207–395 of *P. falciparum* NF54 CS protein (residues 5–193 of SEQ ID NO: 3);

d) Gly;

e) Pro-Val-Thr-Asn from hepatitis B Pre $S_2$ protein; and f) a stretch of 226 amino acids specifying the S protein of hepatitis B virus.

39. A numeric lipoprotein particle comprising the hybrid protein of claim 38 and HBsAg.

40. The particle according to claim 39 wherein the ratio of hybrid protein to S protein is 1:4.

41. A vaccine comprising an immunoprotective amount of a protein according to claim 38 in admixture with a suitable diluent or carrier.

42. The vaccine according to claim 41 additionally comprising one or more of the group consisting of 3-deacylated monophosphoryl lipid A, alum, saponins and an oil and water emulsion.

43. A method of vaccinating a patient susceptible to Plasmodium infections comprising administering an effective amount of the vaccine according to claim 41.

* * * * *

UNITED STATES PATENT AND TRADEMARK OFFICE
CERTIFICATE OF CORRECTION

PATENT NO : 5,928,902
DATED : July 27, 1999
INVENTOR(S) : De Wilde, *et al.*

It is certified that error appears in the above-identified patent and that said Letters Patent are hereby corrected as shown below:

In the Claims:

Claim 39, first line, "numeric", should read, -- multimeric --.

Signed and Sealed this

Third Day of April, 2001

*Attest:*

NICHOLAS P. GODICI

*Attesting Officer*      *Acting Director of the United States Patent and Trademark Office*